United States Patent
Garbuzova-Davis et al.

(10) Patent No.: US 11,007,230 B1
(45) Date of Patent: May 18, 2021

(54) PLASMA DERIVED FROM HUMAN UMBILICAL CORD BLOOD FOR THE TREATMENT OF NEURODEGENERATIVE DISORDERS

(71) Applicants: Svitlana Garbuzova-Davis, Tampa, FL (US); Jared Carl Ehrhart, Tampa, FL (US); Paul R. Sanberg, Spring Hill, FL (US)

(72) Inventors: Svitlana Garbuzova-Davis, Tampa, FL (US); Jared Carl Ehrhart, Tampa, FL (US); Paul R. Sanberg, Spring Hill, FL (US)

(73) Assignees: University of South Florida, Tampa, FL (US); Saneron CCEL Therapeutics, Inc., Tampa, FL (US)

( * ) Notice: Subject to any disclaimer, the term of this patent is extended or adjusted under 35 U.S.C. 154(b) by 109 days.

(21) Appl. No.: 15/250,239

(22) Filed: Aug. 29, 2016

Related U.S. Application Data

(60) Provisional application No. 62/211,478, filed on Aug. 28, 2015.

(51) Int. Cl.
| | |
|---|---|
| *A61K 35/51* | (2015.01) |
| *A61K 35/28* | (2015.01) |
| *A61K 35/12* | (2015.01) |

(52) U.S. Cl.
CPC .............. *A61K 35/51* (2013.01); *A61K 35/28* (2013.01); *A61K 2035/124* (2013.01)

(58) Field of Classification Search
CPC ... A61K 35/51; A61K 35/28; A61K 2035/124
See application file for complete search history.

(56) References Cited

U.S. PATENT DOCUMENTS

| | | |
|---|---|---|
| 4,382,089 A | 5/1983 | Haskell et al. |
| 6,787,143 B1 | 9/2004 | Schenk |

(Continued)

FOREIGN PATENT DOCUMENTS

WO   2006/005802 A1   1/2006

OTHER PUBLICATIONS

T Fietz, WE Berdel, H Rieder, B Reufi, H Hopp, E Thiel and WU Knauf, Culturing human umbilical cord blood: a comparison of mononuclear vs CD34+selected cells, 1999, Bone Marrow Transplantation, vol. 23, pp. 1109-1115.*

(Continued)

*Primary Examiner* — Michelle F. Paguio Frising
*Assistant Examiner* — Trent R Clarke
(74) *Attorney, Agent, or Firm* — Michele L. Lawson; Smith & Hopen, P.A.

(57) ABSTRACT

Amyotrophic lateral sclerosis (ALS) is a progressive neurodegenerative disease characterized by degeneration of motor neurons in the spinal cord and brain. Increasing evidence shows autoimmune mechanisms likely promote disease progression. Human umbilical cord blood (hUCB) derived plasma is rich in cytokines and growth factors that are required for growth and survival of cells during hematopoiesis. hUCB plasma attenuated the hyperactive response (Group III) and potentiated the normal response in Group I ALS patients, but did not alter that of the non-responders to PHA (Group II). The elevated activity of caspase 3/7 observed in the MNCs from ALS patients was significantly reduced by hUCB plasma treatment. The ability of hUCB plasma to modulate the mitogen cell response and reduce caspase activity suggest that the use of hUCB plasma alone, or with stem cells, may prove useful as a therapeutic in ALS patients.

10 Claims, 16 Drawing Sheets

(56) References Cited

U.S. PATENT DOCUMENTS

| | | | |
|---|---|---|---|
| 2002/0107213 | A1 | 8/2002 | Verlinden |
| 2007/0122902 | A1 | 5/2007 | Lee et al. |
| 2008/0292597 | A1* | 11/2008 | Steenblock .......... A61K 9/0019 424/93.7 |
| 2010/0150882 | A1* | 6/2010 | Tan .................... A61K 35/16 424/93.7 |
| 2015/0157664 | A1* | 6/2015 | Wyss-Coray .......... A61K 35/16 424/530 |

OTHER PUBLICATIONS

NPL document "Mouse weight", a screenprint of the Jackson Labs webpage at https://www.jax.org/jax-mice-and-services/strain-data-sheet-pages/body-weight-chart-000664 accessed Mar. 1, 2018.*

Daniele Lo Coco, Santino Marchese, Vincenzo La Bella, Tommaso Piccoli, and Albino Lo Coco, The Amyotrophic Lateral Sclerosis Functional Rating Scale Predicts Survival Time in Amyotrophic Lateral Sclerosis Patients on Invasive Mechanical Ventilation, 2007, Chest, vol. 132, pp. 64-69.*

T. Philips, J.D. Rothstein, Glial cells in amyotrophic lateral sclerosis, 2014, Experimental Neurology, vol. 262, pp. 111-120.*

Aloisi, Francesaca et al. Regulation of T-Cell responses by CNS antigen-presenting cells: different roles for microglia and astrocytes. Immunology Today, 2000. Elsevier Science, Ltd.

Bussiere, Thierry et al. Morphological Characterization of Thioflavin-S-Positive Amyloid Plaques in Transgenic Alzheimer Mice and Effect of Passive Abeta Immunotherapy on Their Clearance. American Journal of Pathology, vol. 165, No. 3. Sep. 2004.

Calingasan, Noel et al. Identification of CD40 in Alzheimer's disease and in animal models of Alzheimer's disease and brain injury. Neurobiology of Aging 23 (2002) 31-39.

Chen, Jieli et al. Intravenous Administration of Human Umbilical Cord Blood Reduces Behavioral Deficits After Stroke in Rats. Journal of the American Stroke Association. Stroke 2001; 32; 2682-2688.

Christie, Richard et al. Structural and Functional Disruption of Vascular Smooth Muscle Cells in a Transgenic Mouse Model of Amyloid Angiopathy. American Journal of Pathology, vol. 158, No. 3, Mar. 2001. pp. 1065-1071.

Cohen, D.L. et al. Amyloid-Beta Protein Angiopathies Masquerading as Alzheimer's Disease? Annals New York Academy of Sciences, pp. 390-395.

Cole, Greg et al. NSAID and Antioxidant Prevention of Alzheimer's Disease. Lessons from in Vitro and Animal Models. Ann. N.Y. Acad. Sci. 1035: 68-84 (2004).

DeMattos, Ronald et al. Brain to Plasma Amyloid-Beta Efflux: a Measure of Brain Amyloid Burden in a Mouse Model of Alzheimer's Disease. Science, Mar. 22, 2002, vol. 295, pp. 2264-2267.

Desideri, Giovambaffista et al. Enhanced soluble CD40 ligand and Alzheimer's disease: Evidence of a possible pathogenetic role. Neurobiology of Aging 29 (2008) 348-356.

DiCarlo, Giovanni et al. Intrahippocampal LPS injections reduce ABeta load in APP+PS1 transgenic mice. Neurobiology of Aging 22 (2001) 1007-1012.

Ende, Norman et al. Human Umbilical Cord Blood Cells Ameliorate Alzheimer's Disease in Transgenic Mice a Brief Report. Journal of Medicine, 2001, PJD Publications Limited. pp. 241-247.

Ende, Norman et al. Parkinson's Disase Mice and Human Umbilical Cord Blood. Journal of Medicine, vol. 33, Nos. 1-4, 2002. pp. 173-180.

Garbuzova-Davis et al. Maternal transplantation of human umbilical cord blood cells provides prenatal therapy in Sanfilippo type B mouse model. The FASEB Journal express article 10.1096/fj.05-4684fje. Published online Jan. 9, 2006.

Grewal, Iqbal et al. CD40 and CD154 in Cell-Mediated Immunity. Annu. Rev. Immunol. 1998, 16:111-35.

Henning, Robert et al. Human Umbilical Cord Blood Mononuclear Cells for the Treatment of Acute Myocardial Infarction. Cell Transplantation, vol. 13, pp. 729-739, 2004.

Holcomb, Leigh et al. Accelerated Alzheimer-type phenotype in transgenic mice carrying both mutant amyloid precursor protein and presenilin 1 transgenes. Nature Medicine, vol. 4, No. 1, Jan. 1998. pp. 97-100.

In't Veld et al. Antihypertensive drugs and incidence of dementia: the Rotterdam Study. Neurobiology of Aging 22 (2001) 407-412.

International Search Report issued by the International Searching Authority dated Feb. 13, 2009 for related International Patent Application No. PCT/US08/73265.

Johnson-Wood, K et al. Amyloid precursor protein processing and ABeta42 deposition in a transgenic mouse model of Alzheimer disease. Proc. Natl Acad. Sci. USA, vol. 94, pp. 1550-1555, Feb. 1997.

Lazarini, Francoise et al. Role of the Alpha-Chemokine Stromal Cell-Dervice Factor (SDF-1) in the Developing and Mature Central Nervous System, GLIA, 2003, vol. 42, pp. 139-148.

Li, Ling et al. Association of Aortic Atherosclerosis with Cerebral Beta-Amyloidosis and Learning Deficits in a Mouse Model of Alzheimer's Disease. American Journal of Pathology, vol. 163, No. 6, Dec. 2003. pp. 2155-2164.

Lim, G.P. et al. Ibuprofen effects on Alzheimer pathology and open field activity in APPsw transgenic mice. Neurobiology of Aging 22 (2001) 983-991.

Lue, Lih-Fen et al. Modeling Alzheimer's Disease Immune Therapy Mechanisms: Interactions of Human Postmortem Microglia with Antibody-Opsonized Amyloid Beta Peptide. Journal of Neuroscience Research 70:599-610 (2002).

Mackey, Matthew et al. The role of CD40/CD154 interactions in the priming, differentiation, and effector function of helper and cytotoxic T cells. Journal of Leukoctye Biology, vol. 63, Apr. 1998. pp. 418-428.

Malm, Tarja et al. Bone-marrow-derived cells contribute to the recruitment of microglial cells in response to beta-amyloid deposition in APP/PS1 double transgenic Alzheimer mice. Neurobiology of Disease, 18 (2005) 134-142.

McGreer, Patrick et al. Immunotherapy for Alzheimer's Disease. Sci. Aging Knowl. Environ., Jul. 7, 2004, vol. 2004, Issue 27, p. pe29.

McGowan, E. et al. Amyloid Phenotype Characterization of Transgenic Mice Overexpressing both Mutant Amyloid Precursor Protein and Mutant Presenilin 1 Transgenes. Neurobiology of Disease 6, 231-244 (1999).

Mitrasinovic, Olivera et al. Macrophage colony stimulating factor promotes phagocytosis by murine microglia. Neuroscience Letters 344 (2003) 185-188.

Mori, Takashi et al. Arundic Acid Ameliorates Cerebral Amyloidosis and Gliosis in Alzheimer Transgenic Mice. The Journal of Pharmacology and Experimental Therapeutics, 2006, vol. 318, No. 2, pp. 571-578.

Nakahata, Tatsutoshi et al. Hemopoietic Colony-forming Cells in Umbilical Cord Blood with Extensive Capability to Generate Mono- and Multipotential Hemopoietic Progenitors. J. Clin. Invest. vol. 70, Dec. 1982. pp. 1324-1328.

Newman, Mary et al. Human Umbilical Cord Blood (HUCB) Cells for Central Nervous System Repair. Neurotoxicity Research, 2003, vol. 5(5). pp. 355-368.

Nguyen, Vince et al. Post-transcriptional inhibition of CD40 gene expression in microglia by transforming growth factor-beta. Eur. J. Immunol. 1998. 28:2537-2548.

Nikolic, William et al. Transcutaneous Beta-amyloid immunization reduces cerebral Beta-amyloid deposits without T cell infiltration and microhemmorrhage. PNAS, Feb. 13, 2007, vol. 104, No. 7, pp. 2507-2512.

Nikolic, William et al. Peripherally Administered Human Umbilical Cord Blood Cells Reduce Parenchymal and Vascular Beta-Amyloid Deposits in Alzheimer Mice. Stem Cells and Development 17:1-17 (2008).

Roach, J. Todd et al. Behavioral effects of CD40-CD40L pathway disruption in aged PSAPP mice. Brain Research 1015 (2004) 161-168.

(56) References Cited

OTHER PUBLICATIONS

Rothe, Mike et al. I-TRAF is a novel TRAF-interacting protein that regulates TRAF-mediated signal transduction. Proc. Natl. Acad. Sci. USA, vol. 93, pp. 8241-8246, Aug. 1996.
Sabbagh, Marwan et al. Amyloid-Beta and Treatment Opportunities for Alzheimer's Disease. Journal of Alzheime's Disease 2 (2000) 231-259.
Sanberg, Paul et al. Umbilical Cord Blood-Derived Stem Cells and Brain Repair, Ann. N.Y. Acad. Sci., 2005, vol. 1049, pp. 67-83.
Servet-Delprat, Christine et al. Flt3+ macrophase precursors commit sequentially to osteoclasts, dendritic cells and microglia. BMC Immunology 2002, 3.
Suen, Yu et al. Decreased Macrophage Colony-Stimulating Factor mRNA Expression from Activated Cord Versus Adult Mononuclear Cells: Altered Posttranscriptional Stability. Blood, vol. 84, No. 12 (Dec. 15, 1994), pp. 4269-4277.
Suen, Yu et al. Regulation of Interleukin-11 Protein and mRNA Expression in Neonatal and Adult Fibroblasts and Endothelial Cells. Blood, vol. 84, No. 12 (Dec. 15, 1994), pp. 4125-4134.
Szekely, Christine et al. Nonsteroidal Anti-Inflammatory Drugs for the Prevention of Alzheimer's Disease: A Systematic Review, Neuroepidemiology, 2004, vol. 23, pp. 159-169.
Tan, Jun et al. CD40-CD40L Interaction in Alzheimer's Disease, Curr. Opin. Pharmacol., 2002, vol. 2, pp. 445-451.
Tan, J. et al. Induction of CD40 on human endothelial cells by Alzheimer's Beta-amyloid peptides. Brain Research Bulletin, vol. 50, No. 2, 1999, pp. 143-148.
Tan, Jun et al. Injection of Complementary DNA Encoding Interleukin-12 Inhibits Tumor Establishment at a Distant Site in a Murine Renal Carcinoma Model. Cancer Research 56, 3399-3403, Aug. 1, 1996.
Tan, Jun et al. Microglial Activation Resulting from CD40-CD40L Interaction After Beta-Amyloid Stimulation. Science 1999, vol. 286, pp. 2352-2355.
Tan, Jun et al. Role of CD40 ligand in amyloidosis in transgenic Alzheimer's mice. Nature Neuroscience, 2002, vol. 5, No. 12, pp. 1288-1293.
Alexianu, The role of immune processes in amyotrophic lateral sclerosis pathogenesis. Rom. J. Neurol. Psychiatry 33 (3-4):215-227; 1995.
Appel, et al., Autoimmunity as an etiological factor in sporadic amyotrophic lateral sclerosis. Adv. Neurol. 68:47-57; 1995.
Baba, et al., Osteogenic potential of human umbilical cord-derived mesenchymal stromal cells cultured with umbilical cord blood-derived autoserum. J. Craniomaxillofac. Surg. 40(8):768-772; 2012.
Broxmeyer, et al., Commentary: a rapid proliferation assay for unknown co-stimulating factors in cord blood plasma possibly involved in enhancement of in vitro expansion and replating capacity of human hematopoietic stem/progenitor cells. Blood Cells 20(2-3):492-497; 1994.
Banerjee, et al., Adaptive immune neuroprotection in G93A-SOD1 amyotrophic lateral sclerosis mice. PLoS One3(7): e2740; 2008.
Beers, et al., CD4+ T cells support glial neuroprotection, slow disease progression, and modify glial morphology in an animal model of inherited ALS. Proc. Natl. Acad. Sci. USA 105(40):15558-15563; 2008.
Bossolasco, et al., Metalloproteinase alterations in the bone marrow of ALS patients. J. Mol. Med. 88(6):553-564; 2010.
Chen et al., CD40/CD40L Dyad in the Inflammatory and Immune Responses in the Central Nervous System. Cellular & Molecular Immunology, vol. 3, No. 3, Jun. 2006.
Chiu, et al., T lymphocytes potentiate endogenous neuroprotective inflammation in a mouse model of ALS. Proc. Natl. Acad. Sci. USA 105(46):17913-17918; 2008.
Coban, et al., Serum anti-neuronal antibodies in amyotrophic lateral sclerosis. Int. J. Neurosci. 123(8):557-562; 2013.
Ding, et al., Human umbilical cord-derived MSC culture: the replacement of animal sera with human cord blood plasma. In Vitro Cell. Dev. Biol. Anim. 49(10):771-777; 2013.

Ferrero, et al., Bone marrow mesenchymal stem cells from healthy donors and sporadic amyotrophic lateral sclerosis patients. Cell Transplant. 17(3):255-266; 2008.
Fiala, et al., IL-17A is increased in the serum and in spinal cord CD8 and mast cells of ALS patients. J. Neuroinflammation 7:76; 2010.
Garbuzova-Davis, et al., Intravenous administration of human umbilical cord blood cells in a mouse model of amyotrophic lateral sclerosis: distribution, migration, and differentiation. J. Hematother. Stem Cell Res. 12(3):255-270; 2003.
Garbuzova-Davis, et al., Human umbilical cord blood treatment in a mouse model of ALS: optimization of cell dose. PLoS One 3(6):e2494; 2008.
Garbuzova-Davis, et al., Multiple intravenous administrations of human umbilical cord blood cells benefit in a mouse model of ALS. PLoS One 7(2):e31254; 2012.
Huang, et al., Human umbilical cord blood plasma can replace fetal bovine serum for in vitro expansion of functional human endothelial colony-forming cells. Cytotherapy 13(6):712-721; 2011.
Kang, et al., Degeneration and impaired regeneration of gray matter oligodendrocytes in amyotrophic lateral sclerosis. Nat. Neurosci. 16(5):571-579; 2013.
Kim, et al., Biological markers of mesenchymal stromal cells as predictors of response to autologous stem cell transplantation in patients with amyotrophic lateral sclerosis: an investigator-initiated trial and in vivo study. Stem Cells 32(10):2724-2731; 2014.
Kim, et al., Ex vivo expansion of human umbilical cord blood-derived T-lymphocytes with homologous cord blood plasma. Tohoku J. Exp. Med. 205(2):115-122; 2005.
Kuzmenok, et al., Lymphopenia and spontaneous autorosette formation in SOD1 mouse model of ALS. J. Neuroimmunol. 172(1-2):132-136; 2006.
Lam, et al., Preclinical ex vivo expansion of cord blood hematopoietic stem and progenitor cells: duration of culture; the media, serum supplements, and growth factors used; and engraftment in NOD/SCID mice. Transfusion 41 (12):1567-1576; 2001.
Lee, et al., The effects of platelet-rich plasma derived from human umbilical cord blood on the osteogenic differentiation of human dental stem cells. In Vitro Cell. Dev. Biol. Anim. 47(2)157-164; 2011.
Lim et al., Ibuprofen Suppresses Plaque Pathology and Inflammation in a Mouse for Alzheimer's Disease. The Journal of Neuroscience, Aug. 1, 2000, 20(15): 5709-5714.
Liu, & Martin, The adult neural stem and progenitor cell niche is altered in amyotrophic lateral sclerosis mouse brain. J. Comp. Neurol. 497(3):468-88; 2006.
Majumdar, et al., Activation of Microglia Acidifies Lysosomes and Leads to Degradation of Alzheimer Amyloid Fibrils. Molecular Biology of the Cell, vol. 18, 1490-1496, Apr. 2007.
Murdock, et al., The dual roles of immunity in ALS: injury overrides protection. Neurobiol. Dis. 77:1-12; 2015.
Newman, et al. Cytokines produced by cultured human umbilical cord blood (HUCB) cells: Implications for brain repair. Experimental Neurology 199 (2006) 201-208.
Niebroj-Dobosz, et al., Auto-antibodies against proteins of spinal cord cells in cerebrospinal fluid of patients with amyotrophic lateral sclerosis (ALS). Folia Neuropathol. 44(3):191-196; 2006.
Pagani, et al., Autoimmunity in amyotrophic lateral sclerosis: past and present. Neurol. Res. Int. 2011:497080; 2011.
Provinciali, et al., Immunity assessment in the early stages of amyotrophic lateral sclerosis: a study of virus antibodies and lymphocyte subsets. Acta Neurol. Scand. 78(6):449-454; 1988.
Rentzos, et al., Interleukin-17 and interleukin-23 are elevated in serum and cerebrospinal fluid of patients with ALS: a reflection of Th17 cells activation? Ada Neurol Scand. 122(6):425-429; 2010.
Rodrigues, et al., The innate and adaptive immunological aspects in neurodegenerative diseases. J. Neuroimmunol. 269(1-2):1-8; 2014.
Saresella, et al., T helper-17 activation dominates the immunologic milieu of both amyotrophic lateral sclerosis and progressive multiple sclerosis. Clin. Immunol. 148(1):79-88; 2013.
Schwartz & Baruch, Breaking peripheral immune tolerance to CNS antigens in neurodegenerative diseases: boosting autoimmunity to fight-off chronic neuroinflammation. J. Autoimmun. 54:8-14; 2014.

(56) References Cited

OTHER PUBLICATIONS

Vajpayee, et al., Evaluation of umbilical cord serum therapy for persistent corneal epithelial defects. Br. J. Ophthalmol. 87(11):1312-1316; 2003.
Yoon, et al., Application of umbilical cord serum eyedrops for the treatment of neurotrophic keratitis. Ophthalmology 114(9):1637-1642; 2007.
Yoon, et al., Application of umbilical cord serum eyedrops for recurrent corneal erosions. Cornea 30(7):744-748; 2011.
International Search Report and Written Opinion issued by the International Searching Authority dated Feb. 13, 2009 for related international patent application No. PCT/US2008/073265.
Restriction Requirement issued by the U.S. Patent Office dated Mar. 11, 2013 for related U.S. Appl. No. 12/706,510.
Restriction Requirement issued by the U.S. Patent Office dated May 13, 2013 for related U.S. Appl. No. 12/706,510.
Non-Final Office Action issued by the U.S. Patent Office dated Jul. 10, 2013 for related U.S. Appl. No. 12/106,510.
Final Office Action issued by the U.S. Patent Office dated Jan. 16, 2014 for related U.S. Appl. No. 12/706,510.
Final Office Action issued by the U.S. Patent Office dated Jul. 31, 2015 for related U.S. Appl. No. 12/765,272.
Final Office Action issued by the U.S. Patent Office dated Sep. 11, 2015 for related U.S. Appl. No. 12/706,510.
Massaad, Cynthia et al. Overexpression of SOD-2 reduces hippocampal superoxide and prevents memory deficits in a mouse model of Alzheimer's disease. PNAS, vol. 106, No. 32, Aug. 11, 2009. pp. 13576-13581.
Restriction Requirement issued by the U.S. Patent Office dated Nov. 2, 2017 for related U.S. Appl. No. 15/195,243.
Tissir, Fadel et al. Expression of the chemokine receptor Cxcr4 mRNA during mouse brain development. Developmental Brain Research, 149 (2004) 63-71.
Togo, Takashi et al. Expression of CD40 in the brain of Alzheimer's disease and other neurological diseases. Brain Research 885 (2000) 117-121.
Town, Terrence et al. Reduced Th1 and enhanced Th2 immunity after immunization with Alzheimer's Beta-amyloid 1-42. Journal of Neuroimmunology 132 (2002) 49-59.
Town, Terrence et al. CD40 signaling and Alzheimer's disease pathogenesis. Neurochemistry International 39 (2001) 371-380.
Townsend, Kirk et al. CD40 signaling regulates innate and adaptive activation of microglia in response to amyloid Beta-peptide. Eur. J. Immunol. 2005. 35: 901-910.
Vendrame, Martina et al. Infusion of Human Umbilical Cord Blood Cells in a Rat Model of Stroke Dose-Dependently Rescues Behavioral Deficits and Reduces Infarct Volume. Stroke, 2004, vol. 35, pp. 2390-2395.
Weggen, Sascha et al. A subset of NSAIDs lower amyloidogenic ABeta42 independently of cyclooxygenase activity. Nature, Nov. 8, 2001, vol. 414, pp. 212-216.
Zandi, Peter et al. Is pharmacological prevention of Alzheimer's a realistic goal? Expert Opin. Pharmacother., 2002, vol. 3, No. 4, pp. 365-380.
Henning, Robert et al. Human Umbilical Cord Blood Progenitor Cells are Attracted to Infarcted Myocardium and Significantly Reduce Myocardial Infarction Size. Cell Transplantation, vol. 15, pp. 647-658, 2006.
Urbich, Carmen et al. Endothelial Progenitor Cells Characterization and Role in Vascular Biology. Circulation Research, Aug. 20, 2004, pp. 343-353.
Nishiyama, Nobuhiro et al. The significant Cardiomyogenic Potential of Human Umbilical Cord Blood-Derived Mesenchymal Stem Cells in Vitro. Stem Cells, Aug. 25, 2007 (8), pp. 2017-2024.
Eve, David et al. Plasma Derived from Human Umbilical Cord Blood Modulates Mitogen-Induced Proliferation of Mononuclear Cells Isolated from the Peripheral Blood of ALS Patients. Cell Transplantation, vol. 25, pp. 963-971, 2016.

\* cited by examiner

PLASMA DERIVED FROM HUMAN UMBILICAL CORD BLOOD FOR THE TREATMENT OF NEURODEGENERATIVE DISORDERS

CROSS REFERENCE TO RELATED APPLICATIONS

This application claims priority to U.S. Provisional Patent Application Ser. No. 62/211,478, entitled "Plasma Derived from Human Umbilical Cord Blood for the Treatment of Neurodegenerative Disorders", filed Aug. 28, 2015, the contents of which are hereby incorporated by reference into this disclosure.

FIELD OF INVENTION

This invention relates to treating neuronal diseases. Specifically, the invention addresses treating neurodegenerative diseases, and/or neuro-inflammatory diseases using cord blood-derived plasma.

BACKGROUND OF THE INVENTION

Amyotrophic lateral sclerosis (ALS) is a progressive degenerative disease involving both upper and lower motor neuron damage in the spinal cord and brain. This disease clinically manifests as muscular weakness and atrophy, which lead to paralysis and death of patients by respiratory failure within 3 to 5 years (Rowland & Shneider, Amyotrophic lateral sclerosis. N. Engl. J. Med. 344(22):1688-1700; 2001). Most cases of ALS are sporadic; the familial (FALS), or genetically linked, form of ALS represents only 10 to 13 percent of all cases (Fiszman, et al., Cu/Zn superoxide dismutase activity at different ages in sporadic amyotrophic lateral sclerosis. J. Neurol. Sci. 162(1):34-37; 1999; Pramatarova, et al., Identification of new mutations in the Cu/Zn superoxide dismutase gene of patients with familial amyotrophic lateral sclerosis. Am. J. Hum. Genet. 56(3): 592-596; 1995). About 20% of FALS cases are the result of mutations in the gene for Cu/Zn superoxide dismutase (SOD1) that are associated with a decrease in SOD1 activity. Over 140 different SOD1 gene mutations have been reported (Andersen, Amyotrophic lateral sclerosis associated with mutations in the CuZn superoxide dismutase gene. Curr. Neurol. Neurosci. Rep. 6(1):37-46; 2006). Available treatments for this disease lack the capacity to arrest disease progression or repair motor neuron function. Cell therapy may be a promising new treatment for ALS.

Human umbilical cord blood (hUCB) may be preferable to other cell sources such as bone marrow due to hUCB cells' low pathogenicity and immune immaturity. The mononuclear cell fraction from human hUCB (MNC hUCB) is relatively rich in multipotent progenitors and has extensive proliferation capacity (Mayani, & Lansdorp, Biology of human umbilical cord blood-derived hematopoietic stem/progenitor cells. Stem Cells 16(3):153-165; 1998; Todaro, et al., Haematopoietic progenitors from umbilical cord blood. Blood Purif. 18(2):144-147; 2000). A number of studies have shown that intravenously administering MNC hUCB (Saneron's proprietary fraction U-CORD-CELL™) into the jugular vein of G93A SOD1 mice delayed the progression of disease and prolonged lifespan, increased motor neuron survival in the cervical/lumbar spinal cord, decreased pro-inflammatory cytokines (interleukin [IL]-1α, IL-1β, tumor necrosis factor [TNF]-α), and restored leukocyte profiles in these mice (Garbuzova-Davis, et al., Multiple intravenous administrations of human umbilical cord blood cells benefit in a mouse model of ALS. PLoS One 7(2):e31254; 2012; Garbuzova-Davis, et al., Human umbilical cord blood treatment in a mouse model of ALS: optimization of cell dose. PLoS One 3(6):e2494; 2008; Garbuzova-Davis, et al., Intravenous administration of human umbilical cord blood cells in a mouse model of amyotrophic lateral sclerosis: distribution, migration, and differentiation. J. Hematother. Stem Cell Res. 12(3):255-270; 2003). While multiple interdependent factors may underlie the pathogenesis of ALS, increasing evidence supports a role for autoimmune mechanisms (Alexianu, The role of immune processes in amyotrophic lateral sclerosis pathogenesis. Rom. J. Neurol. Psychiatry 33(3-4):215-227; 1995; Appel, et al., Autoimmunity as an etiological factor in sporadic amyotrophic lateral sclerosis. Adv. Neurol. 68:47-57; 1995; Coban, et al., Serum anti-neuronal antibodies in amyotrophic lateral sclerosis. Int. J. Neurosci. 123(8):557-562; 2013; Niebroj-Dobosz, et al., Auto-antibodies against proteins of spinal cord cells in cerebrospinal fluid of patients with amyotrophic lateral sclerosis (ALS). Folia Neuropathol. 44(3):191-196; 2006; Pagani, et al., Autoimmunity in amyotrophic lateral sclerosis: past and present. Neurol. Res. Int. 2011:497080; 2011). MNC hUCB were hypothesized to provide neuroprotective and/or trophic effects for motor neurons by modulating the host immune inflammatory system through release of various growth or anti-inflammatory factors. Additionally, hUCB plasma (hUCBP) is a rich source of cytokines and other proteins such as insulin-like growth factor-1 (IGF-1), transforming growth factor (TGF)-β and vascular endothelial growth factor (VEGF) required for growth and survival of hematopoietic stem cells (Broxmeyer, et al., Commentary: a rapid proliferation assay for unknown co-stimulating factors in cord blood plasma possibly involved in enhancement of in vitro expansion and replating capacity of human hematopoietic stem/progenitor cells. Blood Cells 20(2-3): 492-497; 1994; Kim, et al., Ex vivo expansion of human umbilical cord blood-derived T-lymphocytes with homologous cord blood plasma. Tohoku J. Exp. Med. 205(2):115-122; 2005; Lam, et al., Preclinical ex vivo expansion of cord blood hematopoietic stem and progenitor cells: duration of culture; the media, serum supplements, and growth factors used; and engraftment in NOD/SCID mice. Transfusion 41(12):1567-1576; 2001). Moreover, it has been shown that hUCB serum contains more neurotrophic factors (substance P, IGF-1, nerve growth factor [NGF]) compared to the peripheral blood serum effectively used for the treatment of the persistent corneal epithelial defects (Vajpayee, et al., Evaluation of umbilical cord serum therapy for persistent corneal epithelial defects. Br. J. Ophthalmol. 87(11):1312-1316; 2003), neurotrophic keratitis (Yoon, et al., Application of umbilical cord serum eyedrops for the treatment of neurotrophic keratitis. Ophthalmology 114(9):1637-1642; 2007), and recurrent corneal erosion (Yoon, et al., Application of umbilical cord serum eyedrops for recurrent corneal erosions. Cornea 30(7):744-748; 2011). hUCBP has also been used as a replacement for fetal bovine serum in in vitro studies including the expansion of endothelial colony forming cells (Huang, et al., Human umbilical cord blood plasma can replace fetal bovine serum for in vitro expansion of functional human endothelial colony-forming cells. Cytotherapy 13(6):712-721; 2011), mesenchymalstromal cells (MSCs) (Baba, et al., Osteogenic potential of human umbilical cord-derived mesenchymal stromal cells cultured with umbilical cord blood-derived autoserum. J. Craniomaxillofac. Surg. 40(8):768-772; 2012; Ding, et al., Human umbilical cord-derived MSC culture: the replacement of animal sera with human cord blood plasma. In Vitro Cell. Dev. Biol. Anim. 49(10):771-777; 2013), T cells (Kim, et al., Ex vivo expansion of human umbilical cord blood-derived T-lymphocytes with homologous cord blood plasma. Tohoku J. Exp. Med. 205(2):115-122; 2005), and dental stem cells (Lee, et al., The effects of platelet-rich plasma derived from human umbilical cord blood on the osteogenic differentiation of human dental stem cells. In Vitro Cell. Dev. Biol. Anim. 47(2):157-164; 2011), demonstrating that it can exert a favorable influence on stem cells. These results suggest that hUCBP may be effective as an additive to, or substitute for, cells in developing clinically useful protocols for cell-based ALS therapies. Including hUCBP with hUCB cells may add significant therapeutic benefits and plasma alone may also be a useful treatment approach.

The aim of this pre-clinical study was to determine the efficacy of hUCBP on the functional activity of lymphocytes from the peripheral blood of ALS patients. First, hematological profiles were analyzed in the peripheral blood of ALS patients. Second, the mitogen-induced proliferation response of MNCs isolated from the peripheral blood of ALS patients in vitro when cultured with hUCBP were investigated. Finally, the effect of hUCBP upon the apoptotic cell death response in ALS patients was examined.

SUMMARY OF THE INVENTION

Treatment of a neuromotor degenerative disease is disclosed herein. The treatment comprises identifying a patient suffering from a neuromotor degenerative disease, such as through use of the ALS Functional Rating Scale or ALS Functional Rating Scale or ALS Functional Rating Scale or ALS Functional Rating Scale-revised methods. As such, in some embodiments, the neuromotor degenerative disease is amyotrophic lateral sclerosis. The patient is administered plasma derived from umbilical cord blood. In specific variations of the invention the plasma derived from umbilical cord blood is derived from human umbilical cord blood.

Optionally, plasma derived from umbilical cord blood is administered at about 10 ml/kg to about 20 ml/kg. As nonlimiting examples, the plasma derived from umbilical cord blood can be administered at 9 ml/kg, 9.25 m/kg, 9.5 ml/kg, 9.75 ml/kg, 10 ml/kg, 10.25 ml/kg, 10.5 ml/kg, 10.75 ml/kg, 11 ml/kg, 11.25 ml/kg, 11.5 ml/kg, 11.75 ml/kg, 12 ml/kg, 12.25 ml/kg, 12.5 ml/kg, 12.75 ml/kg, 13 ml/kg, 13.25 ml/kg, 13.5 ml/kg, 13.75 ml/kg, 14 ml/kg, 14.1 m/kg, 14.2 ml/kg, 14.3 ml/kg, 14.4 ml/kg, 14.5 ml/kg, 14.6 ml/kg, 114.7 ml/kg, 14.75 ml/kg, 14.8 ml/kg, 14.9 ml/kg, 15 ml/kg, 15.1 ml/kg, 15.2 ml/kg, 15.25 ml/kg, 15.3 ml/kg, 15.4 ml/kg, 15.5 ml/kg, 15.6 ml/kg, 15.7 ml/kg, 15.75 ml/kg, 15.8 ml/kg, 15.9 m/kg, 16 ml/kg, 16.1 ml/kg, 16.2 ml/kg, 16.25 ml/kg, 16.3 ml/kg, 16.4 ml/kg, 16.5 ml/kg, 16.6 ml/kg, 16.7 ml/kg, 16.75 ml/kg, 16.8 ml/kg, 16.9 ml/kg, 17 ml/kg, 17.25 ml/kg, 17.5 ml/kg, 17.75 ml/kg, 18 ml/kg, 18.25 ml/kg, 1 8.5 ml/kg, 18.75 ml/kg, 19 ml/kg, 19.25 ml/kg, 19.5 ml/kg, 19.75 ml/kg, or 20 ml/kg.

Optionally, a therapeutic composition is administered with the plasma derived from umbilical cord blood. The therapeutic composition is riluzole, mesenchymal stem cells, umbilical cord blood cells, or a combination of the aforementioned compounds. In specific variations, the therapeutic composition is umbilical cord blood cells, and may be a mononuclear cell fraction of umbilical cord blood cells. In more specific variations, the composition is a composition of $CD34^+$ cells from the umbilical cord blood cells.

In specific variations, the umbilical cord blood cells are administered at about $1\times10^4$ to about $5\times10^7$ cells, about $1\times10^5$ to about $9\times10^6$ cells, about $2\times10^5$ to about $8\times10^6$ cells, or about $2\times10^5$ cells. Nonlimiting examples include $9\times10^3$ cells, $1.0\times10^4$ cells, $1.25\times10^4$ cells, $1.5\times10^4$ cells, $1.75\times10^4$ cells, $2.0\times10^4$ cells, $2.25\times10^4$, $2.5\times10^4$ cells, $2.75\times10^4$ cells, $3.0\times10^4$ cells, $3.25\times10^4$ cells, $3.75\times10^4$ cells, $4.0\times10^4$ cells, $4.25\times10^4$ cells, $4.5\times10^4$ cells, $4.75\times10^4$ cells, $5.0\times10^4$ cells, $5.25\times10^4$ cells, $5.5\times10^4$ cells, $5.75\times10^4$ cells, $6.0\times10^4$ cells, $6.25\times10^4$ cells, $6.75\times10^4$ cells, $7.0\times10^4$ cells, $7.25\times10^4$ cells, $7.75\times10^4$ cells, $8.0\times10^4$ cells, $8.25\times10^4$ cells, $8.75\times10^4$ cells, $9.0\times10^4$ cells, $9.25\times10^4$ cells, $9.75\times10^4$ cells, $1.0\times10^5$ cells, $1.25\times10^5$ cells, $1.5\times10^5$ cells, $1.75\times10^5$ cells, $2.0\times10^5$ cells, $2.25\times10^5$, $2.5\times10^5$ cells, $2.75\times10^5$ cells, $3.0\times10^5$ cells, $3.25\times10^5$ cells, $3.75\times10^5$ cells, $4.0\times10^5$ cells, $4.25\times10^5$ cells, $4.5\times10^5$ cells, $4.75\times10^5$ cells, $5.0\times10^5$ cells, $5.25\times10^5$ cells, $5.5\times10^5$ cells, $5.75\times10^5$ cells, $6.0\times10^5$ cells, $6.25\times10^5$ cells, $6.75\times10^5$ cells, $7.0\times10^5$ cells, $7.25\times10^5$ cells, $7.75\times10^5$ cells, $8.0\times10^5$ cells, $8.25\times10^5$ cells, $8.75\times10^5$ cells, $9.0\times10^5$ cells, $9.25\times10^5$ cells, $9.75\times10^5$ cells, $1.0\times10^6$ cells, $1.25\times10^6$ cells, $1.5\times10^6$ cells, $1.75\times10^6$ cells, $2.0\times10^6$ cells, $2.25\times10^6$, $2.5\times10^6$ cells, $2.75\times10^6$ cells, $3.0\times10^6$ cells, $3.25\times10^6$ cells, $3.75\times10^6$ cells, $4.0\times10^6$ cells, $4.25\times10^6$ cells, $4.5\times10^6$ cells, $4.75\times10^6$ cells, $5.0\times10^6$ cells, $5.25\times10^6$ cells, $5.5\times10^6$ cells, $5.75\times10^6$ cells, $6.0\times10^6$ cells, $6.25\times10^6$ cells, $6.75\times10^6$ cells, $7.0\times10^6$ cells, $7.25\times10^6$ cells, $7.75\times10^6$ cells, $8.0\times10^6$ cells, $8.25\times10^6$ cells, $8.75\times10^6$ cells, and $9.0\times10^6$ cells.

Alternatively, the umbilical cord blood cells are administered at about $0.1\times10^6$ cells/kg to about $10\times10^8$ cells/kg, about $0.5\times10^6$ cells/kg to about $5\times10^8$ cells/kg, or about $1\times10^7$ cells/kg to about $2\times10^8$ cells/kg. Nonlimiting examples include $1.0\times10^5$ cells/kg, $1.25\times10^5$ cells/kg, $1.5\times10^5$ cells/kg, $1.75\times10^5$ cells/kg, $2.0\times10^5$ cells/kg, $2.25\times10^5$, $2.5\times10^5$ cells/kg, $2.75\times10^5$ cells/kg, $3.0\times10^5$ cells/kg, $3.25\times10^5$ cells/kg, $3.75\times10^5$ cells/kg, $4.0\times10^5$ cells/kg, $4.25\times10^5$ cells/kg, $4.5\times10^5$ cells/kg, $4.75\times10^5$ cells/kg, $5.0\times10^5$ cells/kg, $5.25\times10^5$ cells/kg, $5.5\times10^5$ cells/kg, $5.75\times10^5$ cells/kg, $6.0\times10^5$ cells/kg, $6.25\times10^5$ cells/kg, $6.75\times10^5$ cells/kg, $7.0\times10^5$ cells/kg, $7.25\times10^5$ cells/kg, $7.75\times10^5$ cells/kg, $8.0\times10^5$ cells/kg, $8.25\times10^5$ cells/kg, $8.75\times10^5$ cells/kg, $9.0\times10^5$ cells/kg, $9.25\times10^5$ cells/kg, $9.75\times10^5$ cells/kg, $1.0\times10^6$ cells/kg, $1.25\times10^6$ cells/kg, $1.5\times10^6$ cells/kg, $1.75\times10^6$ cells/kg, $2.0\times10^6$ cells/kg, $2.25\times10^6$, $2.5\times10^6$ cells/kg, $2.75\times10^6$ cells/kg, $3.0\times10^6$ cells/kg, $3.25\times10^6$ cells/kg, $3.75\times10^6$ cells/kg, $4.0\times10^6$ cells/kg, $4.25\times10^6$ cells/kg, $4.5\times10^6$ cells/kg, $4.75\times10^6$ cells/kg, $5.0\times10^6$ cells/kg, $5.25\times10^6$ cells/kg, $5.5\times10^6$ cells/kg, $5.75\times10^6$ cells/kg, $6.0\times10^6$ cells/kg, $6.25\times10^6$ cells/kg, $6.75\times10^6$ cells/kg, $7.0\times10^6$ cells/kg, $7.25\times10^6$ cells/kg, $7.75\times10^6$ cells/kg, $8.0\times10^6$ cells/kg, $8.25\times10^6$ cells/kg, $8.75\times10^6$ cells/kg, $9.0\times10^6$ cells/kg, $9.25\times10^6$ cells/kg, $9.75\times10^6$ cells/kg, $1.0\times10^7$ cells/kg, $1.25\times10^7$ cells/kg, $1.5\times10^7$ cells/kg, $1.75\times10^7$ cells/kg, $2.0\times10^7$ cells/kg, $2.25\times10^7$, $2.5\times10^7$ cells/kg, $2.75\times10^7$ cells/kg, $3.0\times10^7$ cells/kg, $3.25\times10^7$ cells/kg, $3.75\times10^7$ cells/kg, $3.8\times10^7$ cells/kg, $4.0\times10^7$ cells/kg, $4.25\times10^7$ cells/kg, $4.5\times10^7$ cells/kg, $4.75\times10^7$ cells/kg, $5.0\times10^7$ cells/kg, $5.25\times10^7$ cells/kg, $5.5\times10^7$ cells/kg, $5.75\times10^7$ cells/kg, $6.0\times10^7$ cells/kg, $6.25\times10^7$ cells/kg, $6.75\times10^7$ cells/kg, $7.0\times10^7$ cells/kg, $7.25\times10^7$ cells/kg, $7.75\times10^7$ cells/kg, $8.0\times10^7$ cells/kg, $8.25\times10^7$ cells/kg, $8.75\times10^7$ cells/kg, $9.0\times10^7$ cells/kg, $9.25\times10^7$ cells/kg, $9.75\times10^7$ cells/kg, $1.0\times10^8$ cells/kg, $1.25\times10^8$ cells/kg, $1.5\times10^8$ cells/kg, $1.75\times10^8$ cells/kg, $2.0\times10^8$ cells/kg, $2.25\times10^8$, $2.5\times10^8$ cells/kg, $2.75\times10^8$ cells/kg, $3.0\times10^8$ cells/kg, $3.25\times10^8$ cells/kg, $3.75\times10^8$ cells/kg, $4.0\times10^8$ cells/kg, $4.25\times10^8$ cells/kg, $4.5\times10^8$ cells/kg, $4.75\times10^8$ cells/kg, $5.0\times10^8$ cells/kg, $5.25\times10^8$ cells/kg, $5.5\times10^8$ cells/kg, $5.75\times10^8$ cells/kg, $6.0\times10^8$ cells/kg, $6.25\times10^8$ cells/kg, $6.75\times10^8$ cells/kg, $7.0\times10^8$ cells/kg, $7.25\times10^8$ cells/kg, $7.75\times10^8$ cells/kg, $8.0\times10^8$ cells/kg, 8.25×10⁸ cells/kg, 8.75×10⁸ cells/kg, 9.0×10⁸ cells/kg, 9.25×10⁸ cells/kg, 9.75×10⁸ cells/kg, and 1.0×10⁹ cells/kg.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1A:
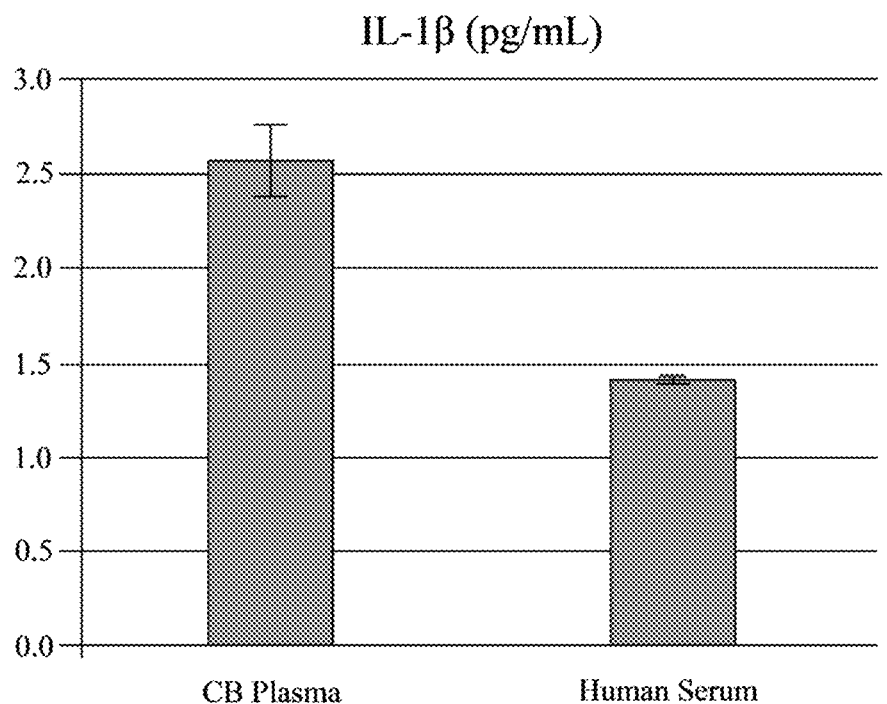
FIG. 1(A) is a graph showing the cytokine profile was assayed on plasma derived from human umbilical cord blood and human adult serum using an ultrasensitive human cytokine panel for IL-1p. Results are plotted as mean±SEM. Statistical significance was determined using two tailed t-tests (* p<0.001).
Figure 1B:
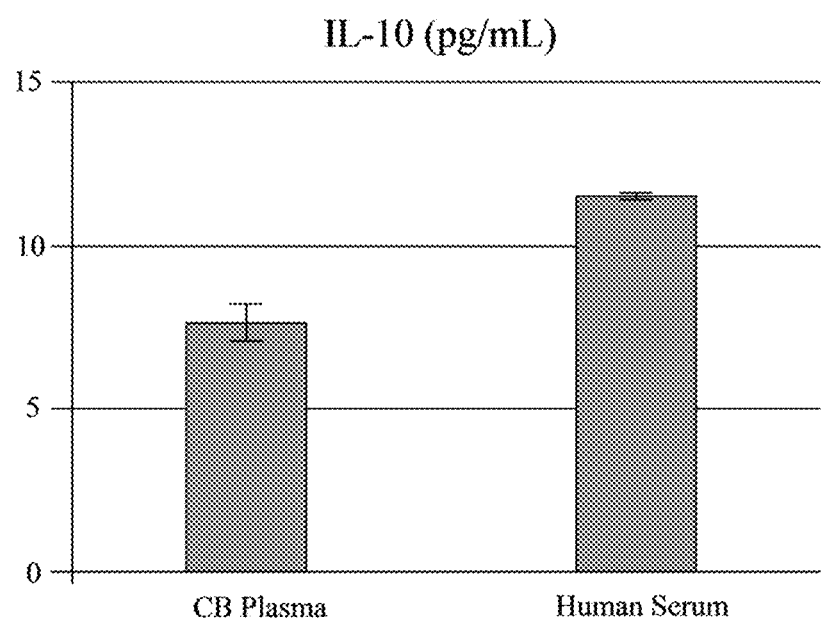
FIG. 1(B) is a graph showing the cytokine profile was assayed on plasma derived from human umbilical cord blood and human adult serum using an ultrasensitive human cytokine panel for IL-10. Results are plotted as mean±SEM. Statistical significance was determined using two tailed t-tests (* p<0.001).
Figure 1C:
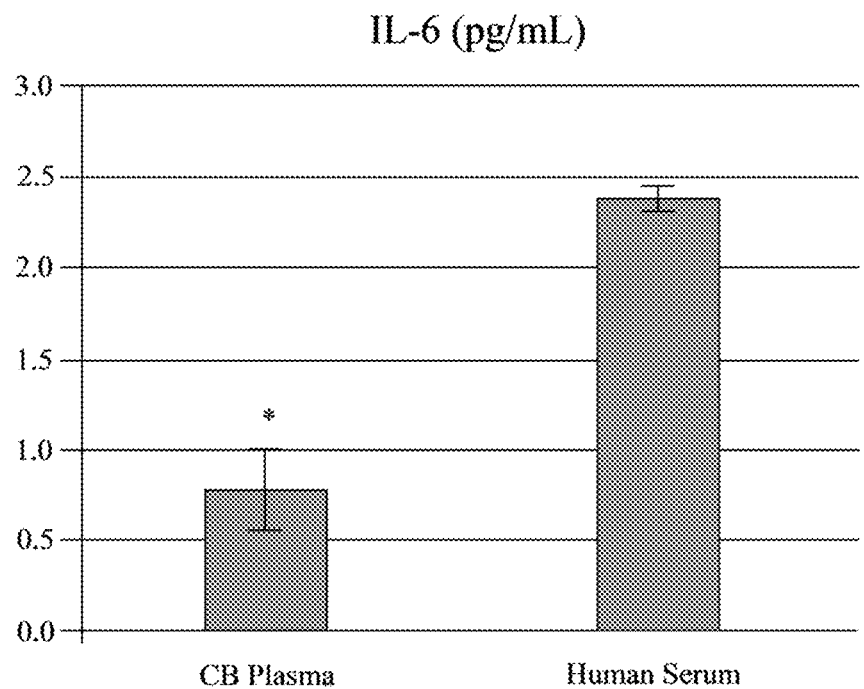
FIG. 1(C) is a graph showing the cytokine profile was assayed on plasma derived from human umbilical cord blood and human adult serum using an ultrasensitive human cytokine panel for IL-6. Results are plotted as mean±SEM. Statistical significance was determined using two tailed t-tests (* p<0.001).
Figure 1D:
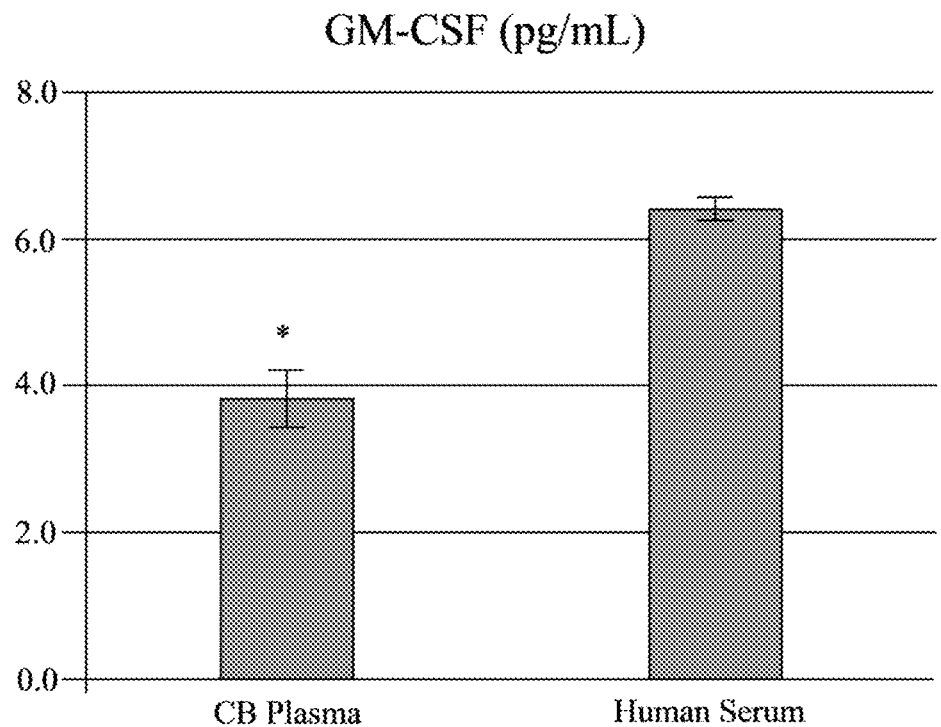
FIG. 1(D) is a graph showing the cytokine profile was assayed on plasma derived from human umbilical cord blood and human adult serum using an ultrasensitive human cytokine panel GM-CSF. Results are plotted as mean±SEM. Statistical significance was determined using two tailed t-tests (* p<0.001).
Figure 1E:
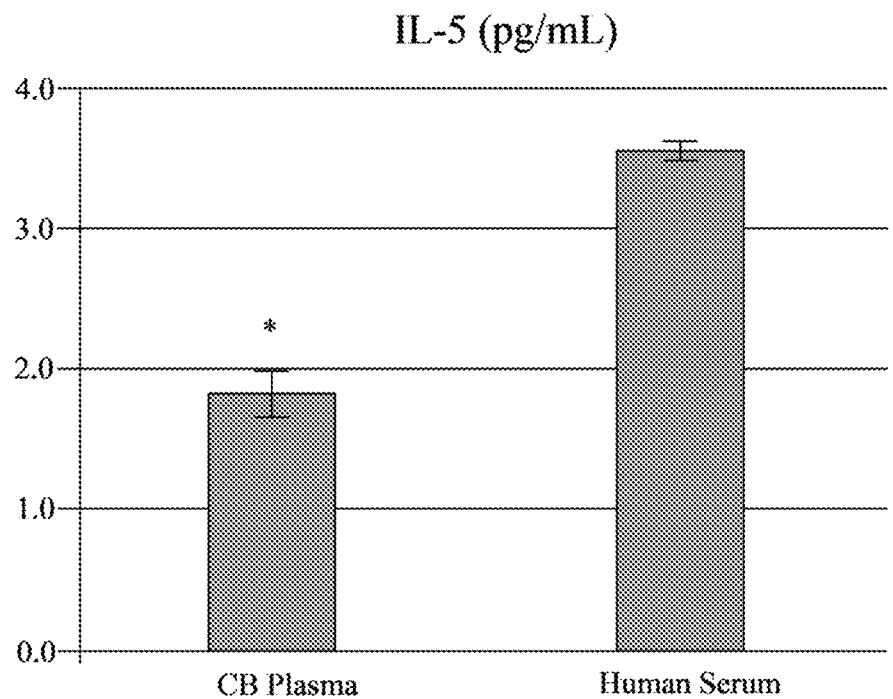
FIG. 1(E) is a graph showing the cytokine profile was assayed on plasma derived from human umbilical cord blood and human adult serum using an ultrasensitive human cytokine panel for IL-5. Results are plotted as mean±SEM. Statistical significance was determined using two tailed t-tests (* p<0.001).
Figure 1F:
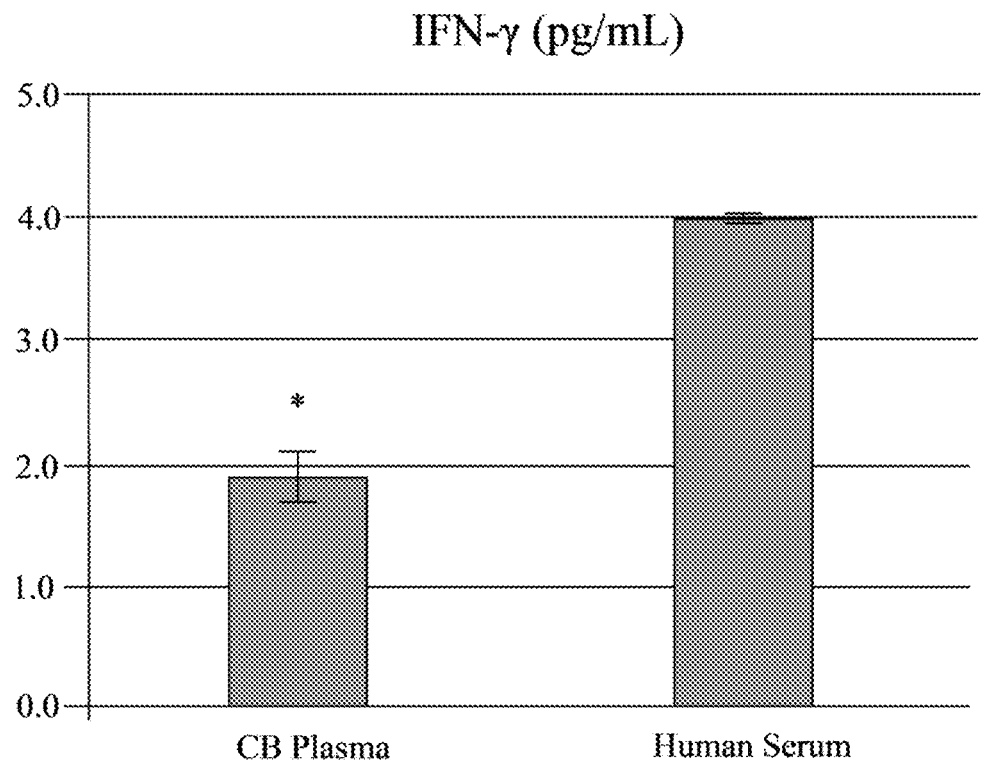
FIG. 1(F) is a graph showing the cytokine profile was assayed on plasma derived from human umbilical cord blood and human adult serum using an ultrasensitive human cytokine panel for IFN-γ. Results are plotted as mean±SEM. Statistical significance was determined using two tailed t-tests (* p<0.001).
Figure 1G:
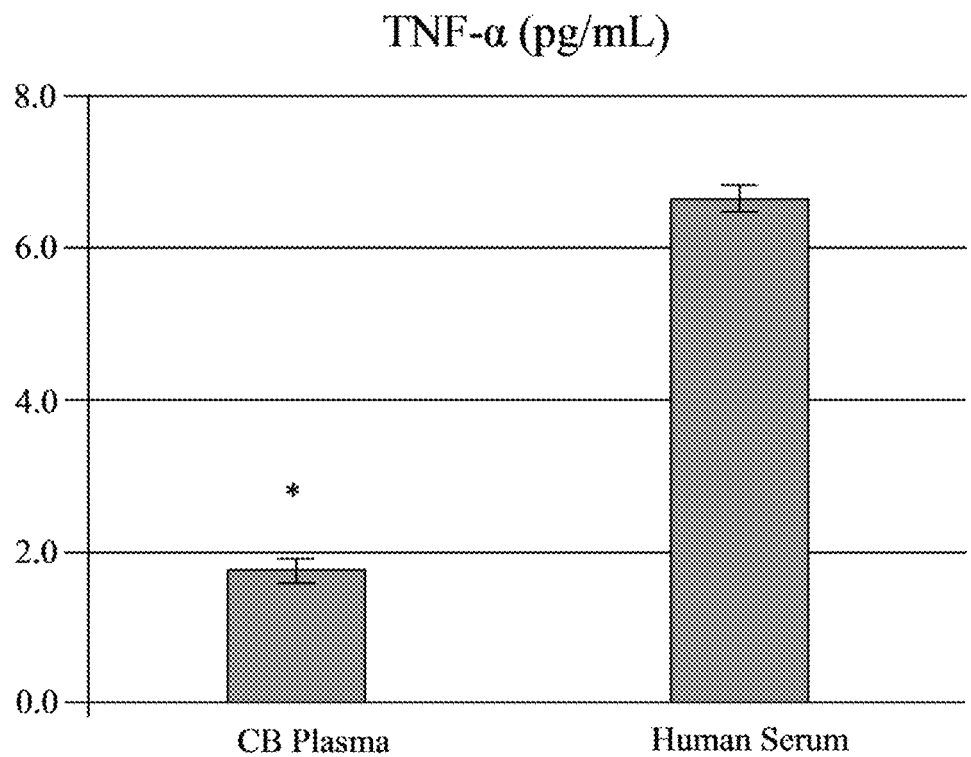
FIG. 1(G) is a graph showing the cytokine profile was assayed on plasma derived from human umbilical cord blood and human adult serum using an ultrasensitive human cytokine panel for TNF-α. Results are plotted as mean±SEM. Statistical significance was determined using two tailed t-tests (* p<0.001).
Figure 1H:
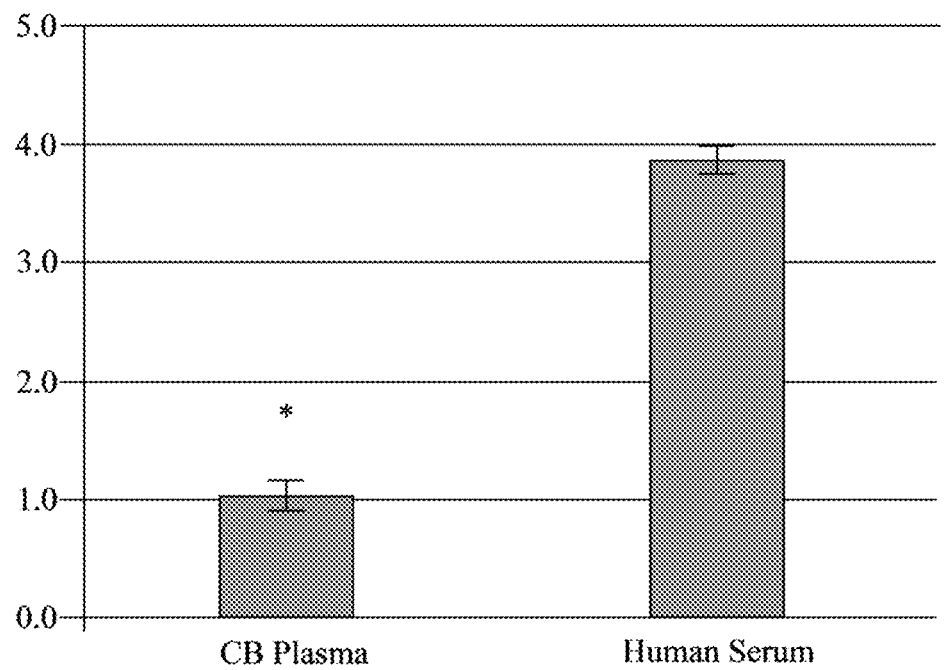
FIG. 1(H) is a graph showing the cytokine profile was assayed on plasma derived from human umbilical cord blood and human adult serum using an ultrasensitive human cytokine panel fir IL-2. Results are plotted as mean±SEM. Statistical significance was determined using two tailed t-tests (* p<0.001).
Figure 1I:
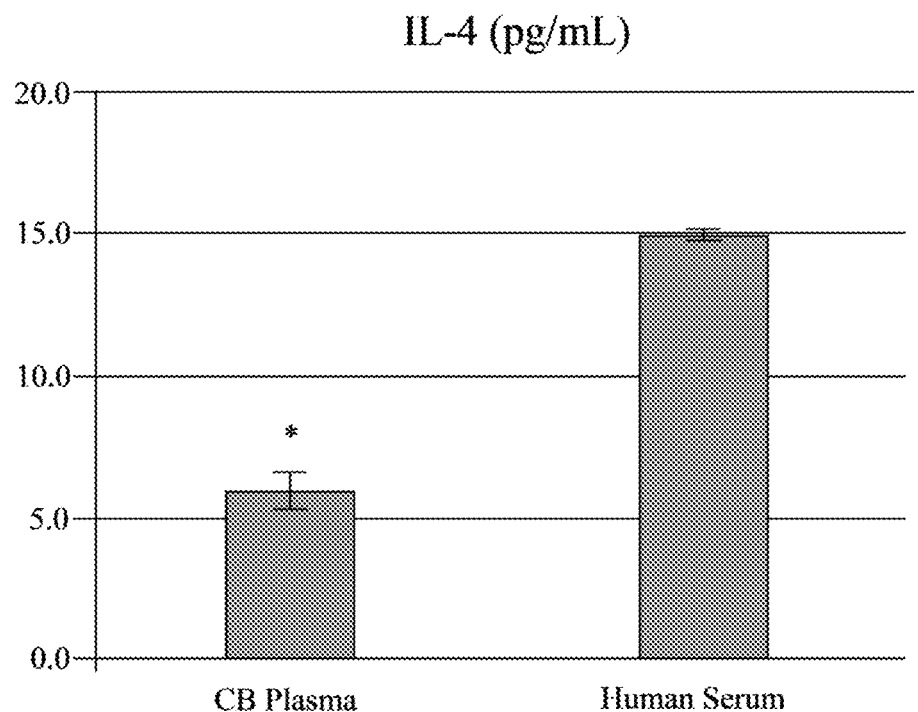
FIG. 1(I) is a graph showing the cytokine profile was assayed on plasma derived from human umbilical cord blood and human adult serum using an ultrasensitive human cytokine panel for IL-4. Results are plotted as mean±SEM. Statistical significance was determined using two tailed t-tests (* p<0.001).

As used herein, "about" means approximately or nearly and in the context of a numerical value or range set forth means±15% of the numerical.

As used herein, "treat", "treatment", "treating", and the like refer to acting upon a condition, such as autoimmune disease or immunotolerance, with an agent depending on the desired effect, to affect the condition by improving or altering it. The improvement or alteration may include an improvement in symptoms or an alteration in the physiologic pathways associated with the condition. "Treatment," as used herein, covers one or more treatments of a condition in a host (e.g., a mammal, typically a human or non-human animal of veterinary interest), and includes: (a) reducing the risk of occurrence of the condition in a subject determined to be predisposed to the condition but not yet diagnosed, (b) impeding the development of the condition, and/or (c) relieving the condition, e.g., causing regression of the condition and/or relieving one or more condition symptoms (e.g., reduce inflammation).

As used herein, the terms "prophylactically treat" or "prophylactically treating" refers completely or partially preventing (e.g., about 50% or more, about 60% or more, about 70% or more, about 80% or more, about 90% or more, about 95% or more, or about 99% or more) a condition or symptom thereof and/or may be therapeutic in terms of a partial or complete cure or alleviation for a condition and/or adverse effect attributable to the condition.

A "pharmaceutically acceptable excipient," "pharmaceutically acceptable diluent," "pharmaceutically acceptable carrier," or "pharmaceutically acceptable adjuvant" means an excipient, diluent, carrier, and/or adjuvant that are useful in preparing a pharmaceutical composition that are generally safe, non-toxic and neither biologically nor otherwise undesirable, and include an excipient, diluent, carrier, and adjuvant that are acceptable for veterinary use and/or human pharmaceutical use. "A pharmaceutically acceptable excipient, diluent, carrier and/or adjuvant" as used in the specification and claims includes one or more such excipients, diluents, carriers, and adjuvants.

The term "therapeutically effective amount" as used herein describes concentrations or amounts of components such as antibodies or other agents which are effective for producing an intended result, including preventing further autoimmune disease or immunotolerance, or treating an autoimmune disease, such as rheumatoid arthritis and asthma, or immunotolerance, such as cancer. Compositions according to the present invention may be used to effect a favorable change on immune cells, whether that change is an improvement, such as stopping or reversing the immune disease, or relieving to some extent one or more of the symptoms of the condition being treated, and/or that amount that will prevent, to some extent, one or more of the symptoms of the condition that the host being treated has or is at risk of developing, or a complete cure of the disease or condition treated.

The term "administration" refers to introducing an agent of the present disclosure into a patient. One preferred route of administration of the agent is oral administration. Another preferred route is intravenous administration. However, any route of administration, such as topical, subcutaneous, peritoneal, intraarterial, inhalation, vaginal, rectal, nasal, introduction into the cerebrospinal fluid, or instillation into body compartments can be used.

As used herein, the term "subject," "patient," or "organism" includes humans and mammals (e.g., mice, rats, pigs, cats, dogs, and horses). Typical patients to which an agent(s) of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like.

The term "umbilical cord blood" is used herein to refer to blood obtained from a neonate or fetus, most preferably a neonate and preferably refers to blood that is obtained from the umbilical cord or the placenta of newborns. Preferably, the umbilical cord blood is isolated from a human newborn. The use of umbilical cord blood as a source of mononuclear cells is advantageous because it can be obtained relatively easily and without trauma to the donor. Umbilical cord blood cells can be used for autologous transplantation or allogenic transplantation, when and if needed. Umbilical cord blood is preferably obtained by direct drainage from the cord an/or by needle aspiration from the delivered placenta at the root and at distended veins. As used herein, the term "cells obtained from umbilical cord blood" refers to cells that are present within umbilical cord blood. In one embodiment, the cells obtained from umbilical cord blood are mononucleated cells that are further isolated from the umbilical cord blood.

Example 1

The human umbilical cord blood plasma (hUCBP) was obtained during isolation of the MNC hUCB (Saneron CCEL Therapeutics Inc.; n=4; 1 male: 3 female). The blood was collected in sterile tubes with heparin (10 units of heparin per 1 mL of blood; BD, Franklin Lakes, N.J., USA) at the time of birth using venipuncture of the umbilical vein. The UCB was diluted (1:1) with sterile phosphate buffered saline (PBS) without $Mg^{2+}$ and $Ca^{2+}$ (Sigma-Aldrich, St. Louis, Mo., USA) at 37° C., and overlaid on 12.5 mL of Ficoll (Ficoll-Paque™ Premium 1.077, GE Healthcare, Cat No. 17-5442-02) in 50 mL sterile centrifuge tubes (BD Falcon, Cat No. 352074, Bedford, Mass., USA). The blood samples were centrifuged at 400×g for 40 min at 26° C. and the mononuclear cell (MNC) layer was transferred with plasma to new 50 mL tubes by using 10 mL serological pipettes (Fisherbrand, Cat No. 13-678-11E, Waltham, Mass., USA). The MNCs with plasma were centrifuged at 440×g for 30 min at 21° C. and the plasma collected from the tube. Plasma was stored at −20° C. The MNCs were washed twice in 30 mL of PBS at 440×g for 13 min at 21° C. The cell numbers and viability were determined using a Vi-CELL Viability Analyzer (Beckman Coulter, Brea, Calif., USA). The MNCs were frozen in Cryopreservation Media (Saneron CCEL Therapeutics, Inc. Tampa, Fla., USA) at $2\times10^6$ cells per vial and stored in liquid nitrogen.

Data are presented as mean±S.E.M. The results were evaluated using ANOVA and Tukey's post hoc test or a paired Student's t-test (Excel; Microsoft, Redmond, Wash., USA). A p value <0.05 was considered significant.

Figure 1J:
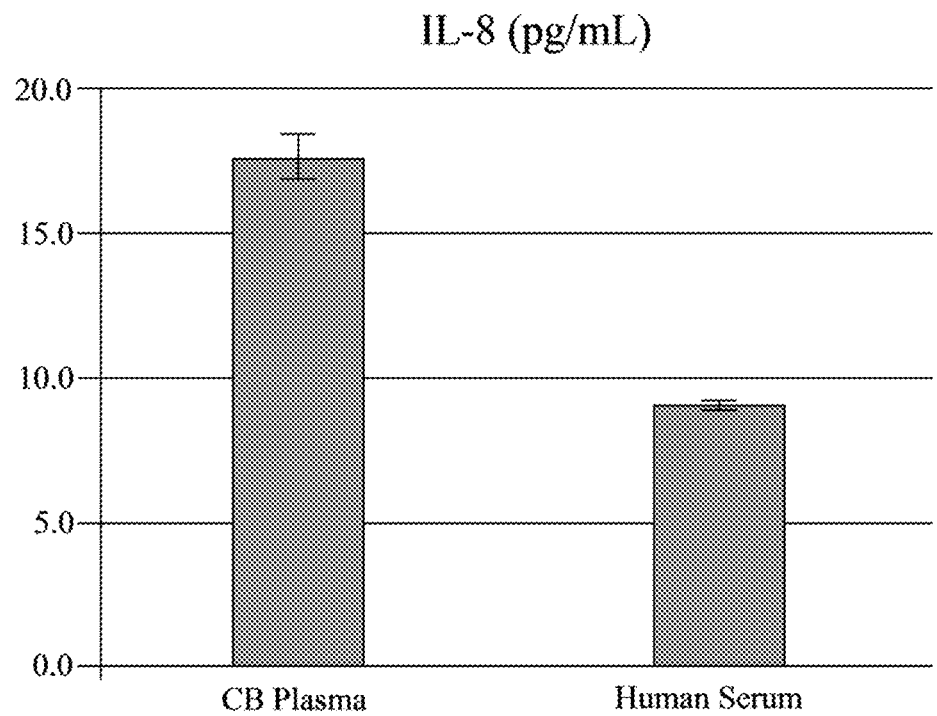
FIG. 1(J) is a graph showing the cytokine profile was assayed on plasma derived from human umbilical cord blood and human adult serum using an ultrasensitive human cytokine panel for IL-8. Results are plotted as mean±SEM. Statistical significance was determined using two tailed t-tests (* p<0.001).

A cytokine profile was performed on the cord blood plasma compared to commercially available adult human serum (Atlanta Biologicals, Cat. No. 540110). Cord blood plasma was found to possess higher levels of the pro- and immunomodulatory cytokines IL-1β and IL-8 compared to adult blood serum, as seen in FIG. 1(A) and FIG. 1(J). However, the cord blood possessed lower levels of IL-10, IL-6, GM-CSF, IL-5, IFN-γ, TNF-α, IL-2, and IL-4 compared to adult blood serum, as seen in FIGS. 1(B), 1(C), 1(D), 1(E), 1(F), 1(G), 1(H), and 1(I). The cytokine levels were significantly different for IL-5, IFN-γ, TNF-α, IL-2, IL-4, GM-CSF, and IL-6, major pro-inflammatory cytokines. This evidences the anti-inflammatory and immunomodulatory properties of cord blood plasma. As such, cord blood plasma is a useful therapeutic agent, and can alternatively be used as a diluent in cell administration in order to provide a beneficial environment for the transplanted cells.

Example 2

A total of twelve ALS patients (11 males and 1 female, mean age 53±2.7 years; range 39-69), with a confirmed diagnosis of "Definite ALS" by a Board-certified neurologist (primary neurologist), and six healthy volunteers (3 males and 3 females, mean age 61.3±4.8 years; range 38-69) were enrolled in the study, as seen in the Table. Eleven patients were Caucasian and one patient was African-American. The healthy volunteers were gender- and age-matched to ALS patients and had no neurological, autoimmune, systemic, or psychiatric diseases. Each participant signed an Informed Consent Form prior to enrolling in the study. The Patient Care Database Form and Medical History Form were completed by each patient and healthy volunteer. A neurological exam was performed upon each study participant. Each study participant was graded on the ALS Functional Rating Scale (ALSFRS; maximum score 40) and ALSFRS-revised (ALSFRS-R; including pulmonary/respiratory function; maximum score 48) using the on-line ALS C.A.R.E. Program (Center for Outcomes Research, Univ. Massachusetts Medical School, Worcester, Mass.) from data collected by the same neurologist.

The ALS patients were divided into three groups based on their ALSFRS assessment scores with four patients in each; Group 1 (late stage; ALSFRS<20; 17.75±0.9), Group 2 (intermediate; 20<ALSFRS<30; 22±0.7),and Group 3 (early stage; ALSFRS score>30; 32.5±1.0). The three groups are significantly different based on ALSFRS and ALSFRS-R scores (p<0.05) but not age, disease duration or time from diagnosis. All healthy control patients scored 40/48 on the ALSFRS/ALSFRS-R assessments.

TABLE 1

ALS patient demographics.

| | All ALS patients | Patients grouped by ALSFRS Score | | | Healthy volunteers |
|---|---|---|---|---|---|
| | | Group 1 | Group 2 | Group 3 | |
| n | 12 | 4 | 4 | 4 | 6 |
| Age (years) mean ± SEM | 53 ± 2.7 (39-69) | 51.3 ± 6.4 (39-69) | 54.0 ± 5.2 (39-63) | 53.8 ± 3.1 (45-59) | 61.3 ± 4.8 (38-69) |
| Sex (male/female) | 11/1 | 4/0 | 3/1 | 4/0 | 3/3 |
| ALSFRS mean ± SEM | 24.1 ± 1.9 (15-35) | 17.8 ± 0.9 (15-19) | 22 ± 0.7 (21-24) | 32.5 ± 1.0 (30-35) | 40.0 ± 0.0 |
| ALSFRS-R mean ± SEM | 30.7 ± 2.1 (21-41) | 24 ± 1.5 (21-27) | 28.5 ± 1.6 (25-32) | 39.5 ± 1.0 (37-41) | 48.0 ± 0.0 |
| Disease onset (months) mean ± SEM | 42.5 ± 7.8 (11-96) | 53.5 ± 13.9 (26-88) | 47 ± 16.8 (20-96) | 27 ± 8.4 (11-49) | NA |
| Months since diagnosis mean ± SEM | 21.5 ± 4.6 (5-53) | 26 ± 6.9 (13-43) | 25.8 ± 9.9 (7-53) | 12.8 ± 7.1 (5-34) | NA |

Peripheral blood (~80 mL) from ALS patients and healthy volunteers was obtained via venipuncture by a nurse. Hematological analysis (complete blood cell [CBC] and white blood cell differential [WBCD] counts) was performed for each blood sample (performed by Quest Diagnostics, Inc., Madison, N.J.). Data are presented as mean±S.E.M. The results were evaluated using ANOVA and Tukey's post hoc test or a paired Student's t-test (Excel; Microsoft, Redmond, Wash., USA). A p value <0.05 was considered significant.

Figure 2:
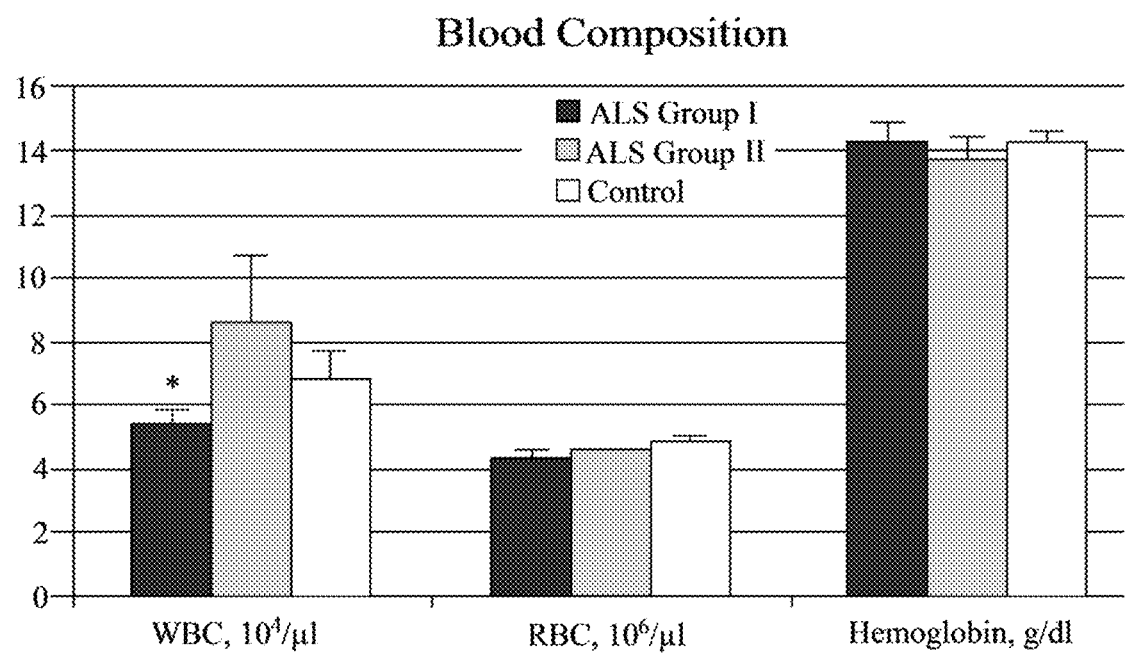
FIG. 2 is a graph showing hematological analysis of the peripheral blood. Seven ALS patients (Group I) had significantly (p=0.0278) low normal WBC counts and two ALS patients (Group II) had higher counts than healthy volunteers. Although, there were no significant differences in RBC counts or hemoglobin level between ALS patients and healthy volunteers, two patients from Group I had low normal RBC (3.9×106/µL and 3.6×106/µL) and hemoglobin level (12.4 g/dL and 12.1 g/dL) compared to reference range for RBC (4.2-5.8×106/L) and hemoglobin (13.2-17.1 g/dL). Significantly fewer lymphocytes (p=0.0255) and elevated neutrophils (p=0.0218) were noted in Group II compared to both Group I and healthy volunteers.
Figure 3:
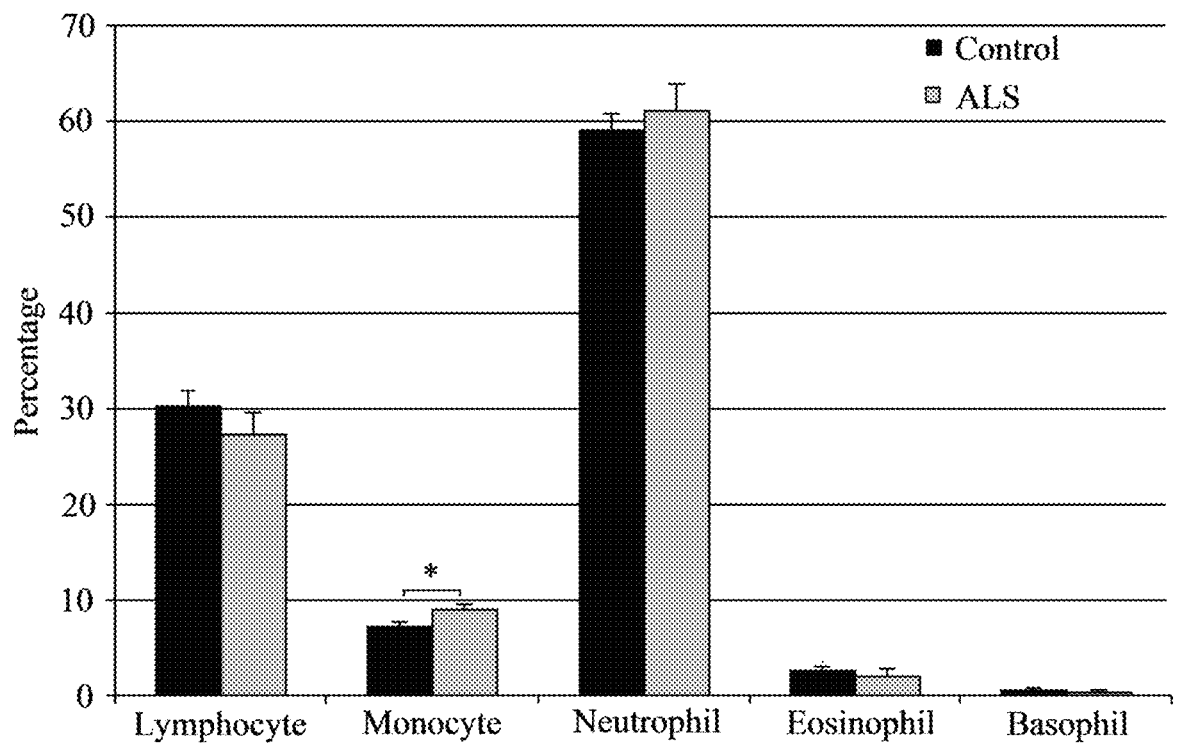
FIG. 3 shows hematological analysis of the peripheral blood. No significant differences in the hematological analysis of the peripheral blood were observed between Amyotrophic lateral sclerosis (ALS) patients (n=10) and healthy volunteers (n=5), except for a significant increase in monocyte number (*p<0.05).

Seven ALS patients (Group I) had significantly (p=0.0278) low normal WBC counts and two ALS patients (Group II) had higher counts than healthy volunteers. Although, there were no significant differences in RBC counts or hemoglobin level between ALS patients and healthy volunteers, two patients from Group I had low normal RBC ($3.9 \times 10^6/\mu L$ and $3.6 \times 10^6/\mu L$) and hemoglobin level (12.4 g/dL and 12.1 g/dL) compared to reference range for RBC ($4.2$-$5.8 \times 10^6/\mu L$) and hemoglobin (13.2-17.1 g/dL). However, in general Group I ALS patients exhibited lower WBC compared to controls, whereas Group II ALS patients exhibited higher WBC counts, as seen in FIG. 2. An analysis of the WBC constituents showed control patient blood contains slightly higher lymphocyte cells and eosinophils, whereas ALS patient possess slightly higher neutrophil counts, and higher monocyte cell counts, as seen in FIG. 3. Of the differences seen, only the alterations in monocyte levels were statistically significant, which were significantly higher in all ALS patients (8.98% vs. 7.3%; p<0.05). However, when the ALS patient population was segregated based on ALSFRS, significantly fewer lymphocytes (p=0.0255) and elevated neutrophils (p=0.0218) were noted in Group II compared to both Group I and healthy volunteers.

Figure 4:
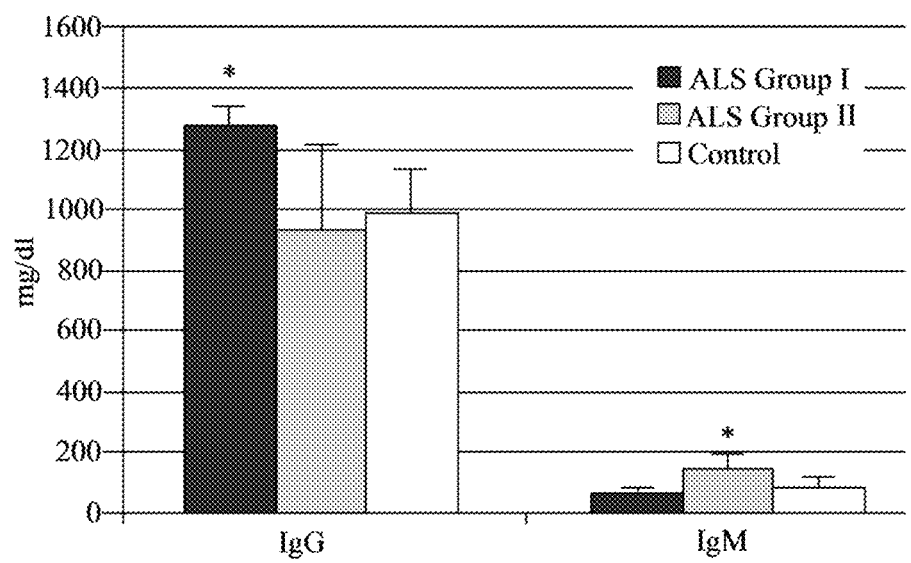
FIG. 4 is a graph showing immunological analysis of the peripheral blood. Levels of IgG were significantly higher in Group I compared to both healthy volunteers (p=0.0364) and Group II (p=0.0511), while the IgM profile was opposite, with significant (p=0.0357) elevation in Group II. Note: Reference ranges for adults: IgG is 654-1618 mg/dL; IgM is 48-271 mg/dL. Reference ranges for cord blood: IgG is 553-1360 mg/dL; IgM is <17 mg/dL

Levels of IgG were significantly higher in Group I compared to both healthy volunteers (p=0.0364) and Group II (p=0.0511), while the IgM profile was opposite, with significant (p=0.0357) elevation in Group II, seen in FIG. 4. By comparison, typically ranges for IgG in healthy adults is 654-1618 mg/dL, and for IgM is 48-271 mg/dL. Additionally, the reference ranges for IgG in cord blood is 553-1360 mg/dL, and for IgM is <17 mg/dL.

Blood smears from each blood sample were fixed in methanol for immunocytochemical analysis of CD4 and CD8 cells. Briefly, the mouse monoclonal antibodies CD4 (ab848) or CD8 (ab17147) (1:200, Abcam PLC, Cambridge, UK) were applied on a slide after 60 min pre-incubation with 10% normal goat serum and Triton X100 in phosphate buffered saline (PBS). After incubating overnight at 4° C., the slides were washed and incubated with goat anti-mouse secondary antibody conjugated to rhodamine (1:1200, Alexa, Molecular Probes) or FITC (1:500, Alexa, Molecular Probes) for 2 hrs at room temperature. Then the slides were rinsed in PBS and coverslipped with Vectashield (DAPI, Vector) and examined under epifluorescence. Counts of CD4 and CD8 positive cells were performed on five representative images from each slide using ImagePro Software. The percentages of CD4 and CD8 positive cells were calculated based upon the total number of DAPI positive cells. Also, routine Giemsa staining was performed for each blood sample.

Figure 5A:
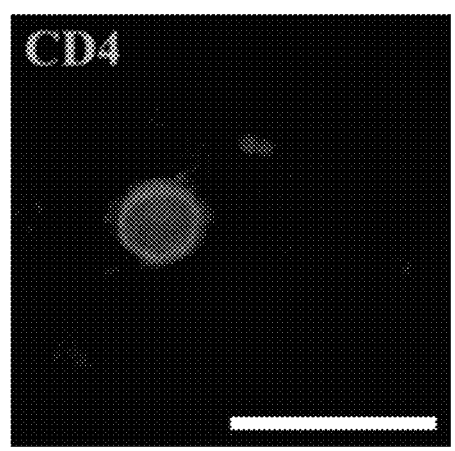
FIG. 5(A) is a microscopic image showing immunocytochemical analysis of CD4. Scale bar in images is 25 µm.
Figure 5B:
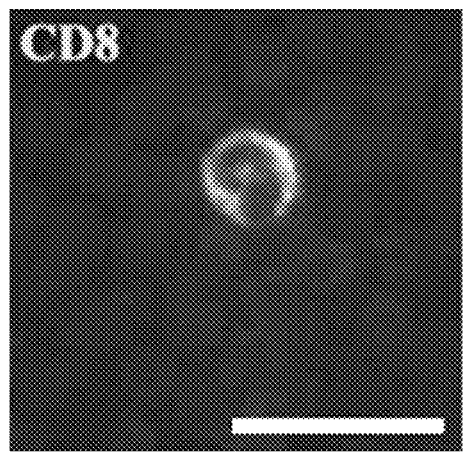
FIG. 5(B) is a microscopic image showing immunocytochemical analysis of CD8. Scale bar in images is 25 µm.

The ratio of CD4 staining, compared to CD8 staining was analyzed. In Group I ALS patients, the ratio of CD4/CD8 was similar to healthy control blood samples (1.63±0.13 for Group I, 1.59±0.09 for control). However, in Group II ALS patients, the ratio of CD4/CD8 was elevated (1.86±0.11), as seen in FIG. 5.

ALS patients showed hematological and immunological differences depending upon the stage of disease. Patients in Group I, as defined by ALSRS, had significantly lower WBC counts and higher IgG levels than patients in Group II. The Group II patients had significantly higher percentages of neutrophils and lower percentages of lymphocytes in WBC, higher IgM levels, and an elevated CD4/CD8 ratio. These results may indicate early stage infections and/or inflammation in the Group II patients Example 3

Fresh peripheral blood from ALS patients and healthy volunteers was collected in sterile tubes with heparin (10 units of heparin per 1 mL of blood; BD, Franklin Lakes, N.J., USA) and diluted (1:1) with sterile phosphate buffered saline (PBS) without $Mg^{2+}$ and $Ca^{2+}$ (Sigma-Aldrich, St. Louis, Mo., USA) at 37° C. Then, 12.5 mL of Ficoll (Histopaque-1077, Sigma-Aldrich, Cat No. 10771) was added into 50 mL sterile centrifuge tubes (BD Falcon, Cat No. 352074, Bedford, Mass., USA). Blood samples diluted in PBS were overlaid on the Ficoll and centrifuged at 400×g for 40 min at 26° C. The MNC layer was transferred with plasma to new 50 mL tubes by using 10 mL serological pipettes (Fisherbrand, Cat No. 13-678-11E, Waltham, Mass., USA). The MNCs were washed twice in 30 mL of PBS at 440×g for 13 min at 21° C. The cell numbers and viability were determined using a Vi-CELL Viability Analyzer (Beckman Coulter, Brea, Calif., USA). The MNCs were frozen in Cryopreservation Media (Saneron CCEL Therapeutics, Inc. Tampa, Fla., USA) at $2 \times 10^6$ cells per vial and stored in liquid nitrogen. Cell samples contained approximately 7.4 million white blood cells per millimeter, 11.6% granulocytes, and 1-4% $CD34^+$ cells.

Cryopreserved MNCs were thawed rapidly at 37° C. then transferred slowly with a pipette into a 15-ml centrifuge tube containing sterile PBS. The cells were centrifuged (400×g/7 min), the supernatant discarded and the process repeated. After the final wash, viability of cells was assessed using the 0.4% trypan blue dye exclusion method prior to culture. The cells ($25 \times 10^3$) were plated in triplicate in 96-well plates (Fisher Brand) with Roswell Park Memorial Institute (RPMI)-1640/10% fetal bovine serum (FBS) (Medium 1; all from Sigma-Aldrich). After 24 hours incubation, phytohemagglutinin (PHA; Sigma-Aldrich) was added to the culture at 1 µg/mL or 10 µg/mL. The cell colonies in the entire well were counted at 24, 48, and 72 hours incubation. The index of stimulation (IS) was determined as the number of induced colonies/number spontaneous colonies in the control wells.

Data are presented as mean±S.E.M. The results were evaluated using ANOVA and Tukey's post hoc test or a paired Student's t-test (Excel; Microsoft, Redmond, Wash., USA). A p value <0.05 was considered significant.

Figure 6:
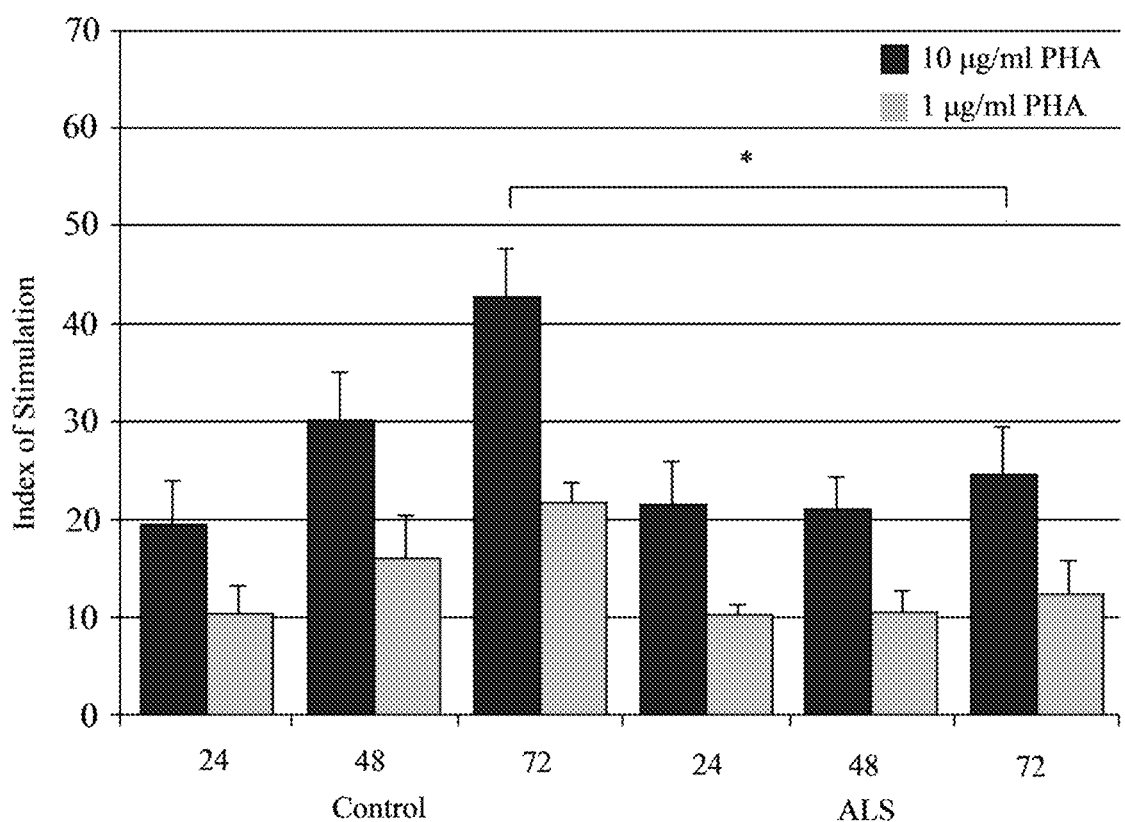
FIG. 6 is a graph showing PHA-induced proliferation of MNCs isolated from peripheral blood in Medium 1 (containing FBS) and Medium 2 (containing hUCBP). The response profile of mononuclear cells (MNCs) from healthy controls (n=5) to phytohemagglutinin (PHA; 10 µg/mL) stimulation when the cells were incubated with Medium 1 (fetal bovine serum [FBS] only containing) showed a normal increasing index of stimulation (IS) with time. However, in ALS patients (n=12), this was not observed. A smaller, but similar effect was seen with the lower dose (1 µg/mL). The 10 µg/mL PHA IS was significantly higher than the 1 g/mL at all time points for both ALS and controls (p<0.05) and the 72 hr 10 g/mL was significantly higher in controls.

The peripheral blood isolated MNCs were cultured in vitro with the mitogen PHA, seen in FIG. 6. There were three different response profiles of MNCs to PHA (10 g/mL) stimulation when the cells were incubated with Medium 1. In healthy control volunteers, the index of stimulation was 32 at 24 h to 50 at 72 h of incubation, and showed apparent linear increases over time. MNCs from some ALS patients was similar, but abnormal extensive proliferation (increased stimulation with a decreasing trend over time) and non-inducible proliferation were observed, from a value of 10 at 24 hours post-treatment to a value of 20 at 72 hours post-treatment for the lower treatment dose (1 µg/mL PHA). Higher dosages (10 µg/mL PHA) display a similar relationship, with values ranging from 20 at 24 hours post-treatment to 40 at 72 hours post-treatment. These trends display a typical time- and dose-dependent increase in response to PHA stimulation (p<0.05; n=5). Dose-dependent effects were seen in ALS patients, as the high-dose PHA stimulation consistently increased the index of stimulation (p<0.05), but no time-dependent increases were observed. At 72 hrs and a dose of 10 g/ml, the control patients' IS was significantly higher than that for the ALS MNCs. Interestingly, low response to PHA at 1 g/mL concentration was found in all ALS patients compared to control healthy volunteers.

Figure 7:
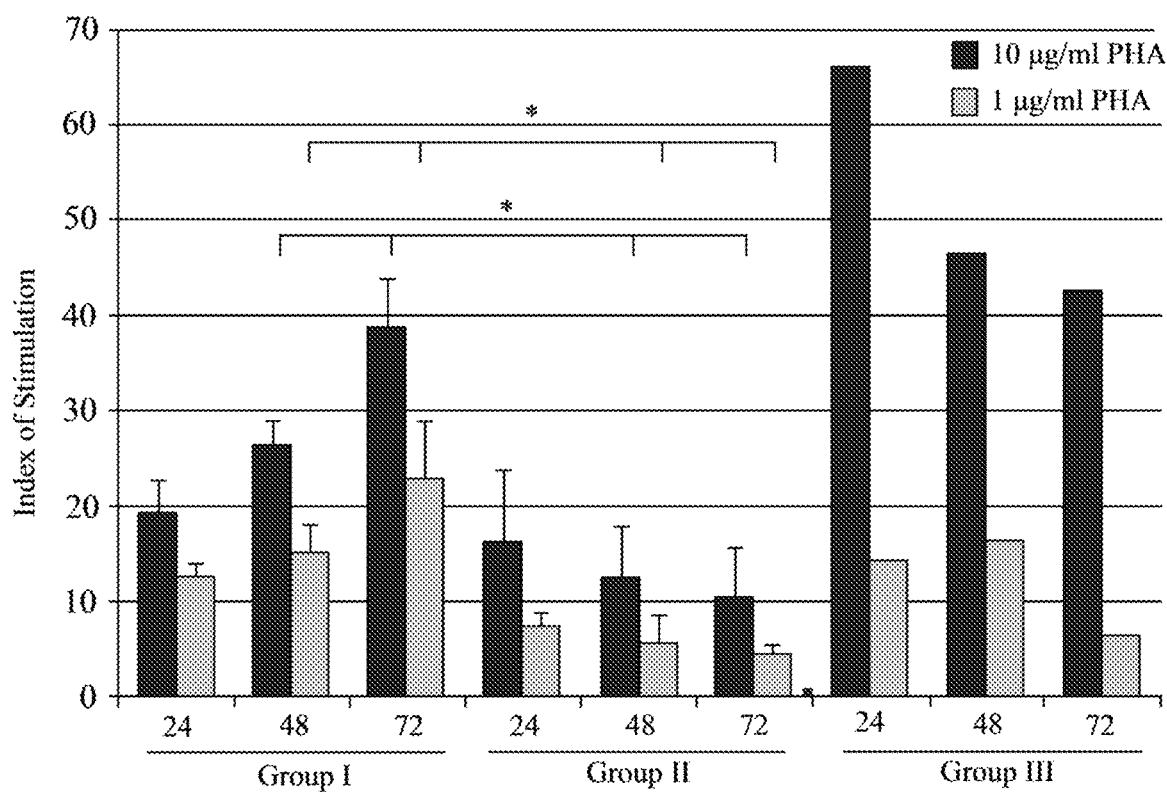
FIG. 7 is a graph showing PHA-induced proliferation of MNCs isolated from peripheral blood in Medium 1 (containing FBS) and Medium 2 (containing hUCBP). Examination of the responses to PHA stimulation revealed that there were three different response profiles for the ALS patients' cells. The IS of MNCs from some ALS patients was similar (Group I; n=5), but abnormal extensive proliferation (increased stimulation with a decreasing trend over time; Group III; n=1) and non-inducible proliferation were also observed (Group II). Group II (n=6) was significantly different from both Group I and controls at both concentrations (* p<0.05) and the 10 g/mL PHA IS was significantly higher than the 1 g/mL at all time points for Group II ALS and control only (p<0.05).

Further analysis of the ALS data revealed three distinct profiles that emerged when the isolated MNCs were incubated with PHA, seen in FIG. 7. The index of stimulation (IS) for some ALS patients was similar to that of controls showing the typical time- and dose-dependent response without significant difference (Group I; n=5). However, abnormal extensive proliferation (an increased stimulation with a decreasing trend over time) was observed in one patient (Group III; this is neither the female patient, the African-American, nor the patient with the lowest ALS score, though it is the oldest patient). Non-inducible proliferation was observed with MNCs isolated from other ALS patients (Group II; n=6). Group II showed a significant dose-dependent response at each time point (p<0.05) and was significantly reduced compared to Group I and controls at 48 and 72 hrs for both concentrations of PHA. Additionally, MNCs isolated from human umbilical cord blood (hUCB) showed little to no cell proliferation with either concentration of PHA used (data not shown). The normal, abnormal extensive proliferation and non-responding patients did not correlate with the three ALSFRS-designated groups. Re-analysis of the previous parameters using this grouping also did not reveal any significant differences. Since Group III only contained one patient, no statistics could be performed using this group.

ALS patients differed in lymphocyte functionality, possible due to differences in immune response. Patients with abnormally extensive cell proliferation (Group III) in response to mitogen (PHA) in vitro probably have autoimmunity impairment while non-inducible proliferation (Group II) may indicate immune deficiency.

Example 4

The hUCB plasma (hUCBP) was obtained during isolation of the MNC hUCB cells, as described previously. The blood was collected in sterile tubes with heparin (10 units of heparin per 1 mL of blood; BD, Franklin Lakes, N.J., USA) at the time of birth using venipuncture of the umbilical vein. The UCB was diluted (1:1) with sterile phosphate buffered saline (PBS) without $Mg^{2+}$ and $Ca^{2+}$ (Sigma-Aldrich, St. Louis, Mo., USA) at 37° C., and overlaid on 12.5 mL of Ficoll (Histopaque-1077, Sigma-Aldrich, Cat No. 10771) in 50 mL sterile centrifuge tubes (BD Falcon, Cat No. 352074, Bedford, Mass., USA). The blood samples were centrifuged at 400×g for 40 min at 26° C. and the mononuclear cell (MNC) layer was transferred with plasma to new 50 mL tubes by using 10 mL serological pipettes (Fisherbrand, Cat No. 13-678-11E, Waltham, Mass., USA). Plasma was stored at −20° C.

Peripheral blood (~80 mL) from was obtained from the ALS patients and healthy volunteer population via venipuncture by a nurse and processed as described in Example 1. Briefly, blood was collected in heparin tubes (BD, Franklin Lakes, N.J., USA) and diluted in PBS without $Mg^{2+}$ and $Ca^{2+}$ (Sigma-Aldrich, St. Louis, Mo., USA) at 37° C., followed by Ficoll extraction (Histopaque-1077, Sigma-Aldrich, Cat No. 10771). The MNCs were washed twice in 30 mL of PBS and MNCs were frozen in Cryopreservation Media (Saneron CCEL Therapeutics, Inc. Tampa, Fla., USA) at $2\times10^6$ cells per vial and stored in liquid nitrogen.

Cryopreserved MNCs, described in Example 3, were thawed rapidly at 37° C. then transferred slowly with a pipette into a 15-ml centrifuge tube containing sterile PBS. The cells were centrifuged (400×g/7 min), the supernatant discarded and the process repeated. Cell viability was determined using trypan blue dye and the cells ($25\times10^3$) plated in triplicate in 96-well plates (Fisher Brand) with RPMI-1640/10% fetal bovine serum (FBS) (Medium 1; all from Sigma-Aldrich), or RPMI-1640/10% hUCBP ABO Rh matched (Medium 2). After 24 hours incubation, phytohemagglutinin (PHA; Sigma-Aldrich) was added to the culture at 1 µg/mL or 10 µg/mL. The cell colonies in the entire well were counted at 24, 48, and 72 hours after addition of PHA. The index of stimulation (IS) was determined as the number of induced colonies/number spontaneous colonies in the control wells.

Data are presented as mean±S.E.M. The results were evaluated using ANOVA and Tukey's post hoc test or a paired Student's t-test (Excel; Microsoft, Redmond, Wash., USA). A p value <0.05 was considered significant.

Figure 8:
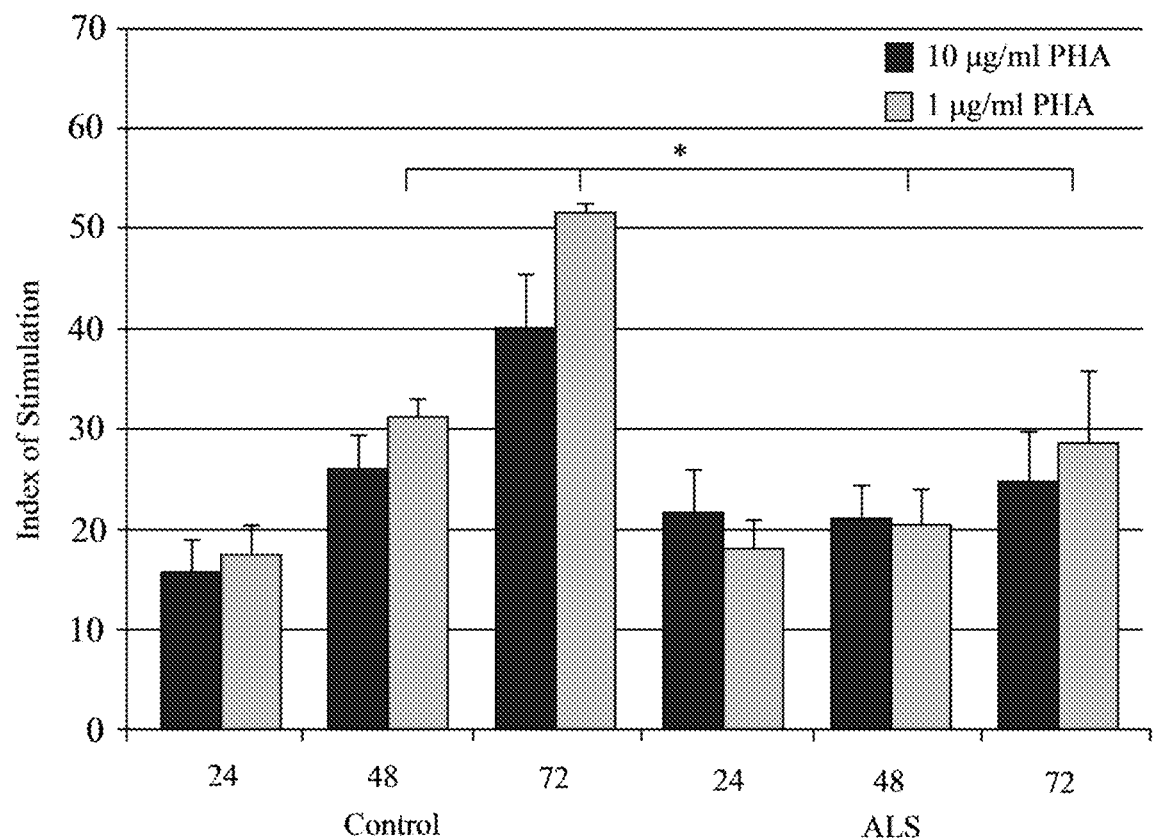
FIG. 8 is a graph showing PHA-induced proliferation of MNCs isolated from peripheral blood in Medium 1 (containing FBS) and Medium 2 (containing hUCBP). When MNCs were cultured in Medium 2 containing hUCB plasma, the proliferation response of cells to PHA (10 g/mL) of ALS patients remained significantly reduced compared to controls (* p<0.05).
Figure 9A:
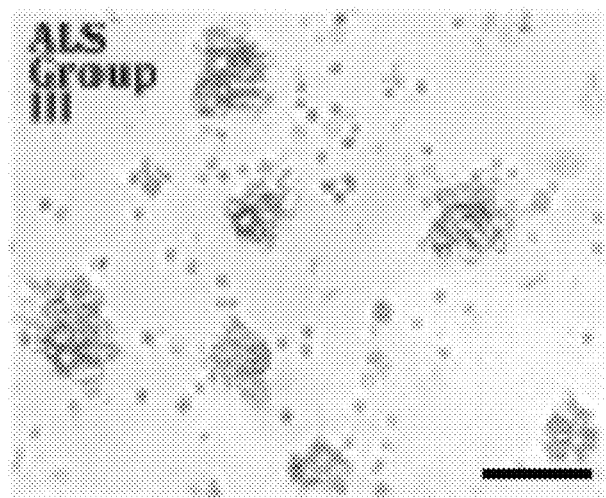
FIG. 9(A) is a microscope image showing PHA-induced proliferation of MNCs isolated from peripheral blood of an ALS patient from Group III, in Medium 1 (containing FBS). Group III; abnormal extensive cell proliferation. Scale bar is 100 μm.
Figure 9B:
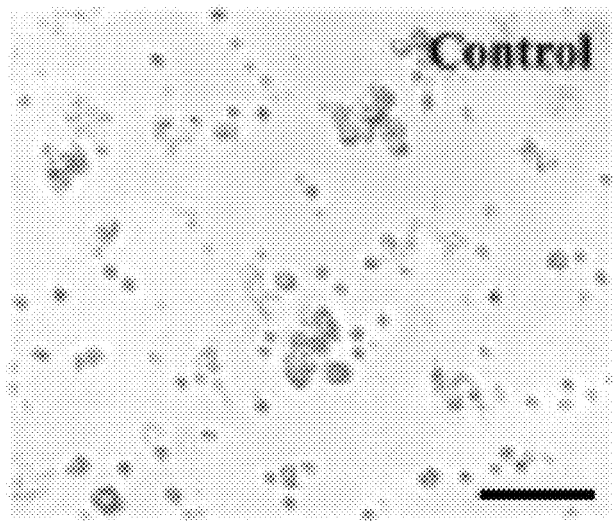
FIG. 9(B) is a microscope image showing PHA-induced proliferation of MNCs isolated from peripheral blood from a healthy control individual, in Medium 1 (containing FBS). Scale bar is 100 μm.
Figure 9C:
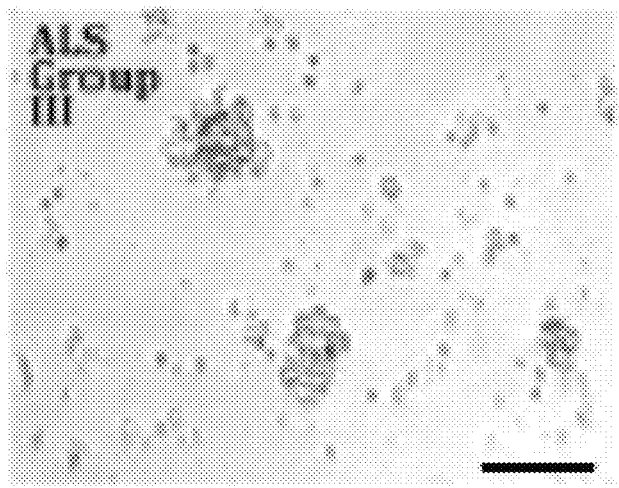
FIG. 9(C) is a microscope image showing PHA-induced proliferation of MNCs isolated from peripheral blood of an ALS patient from Group III, in Medium 2 (containing hUCBP). Images show decreased numbers of colonies in Medium 2 (Group III; abnormal extensive cell proliferation). Scale bar is 100 μm.
Figure 9D:
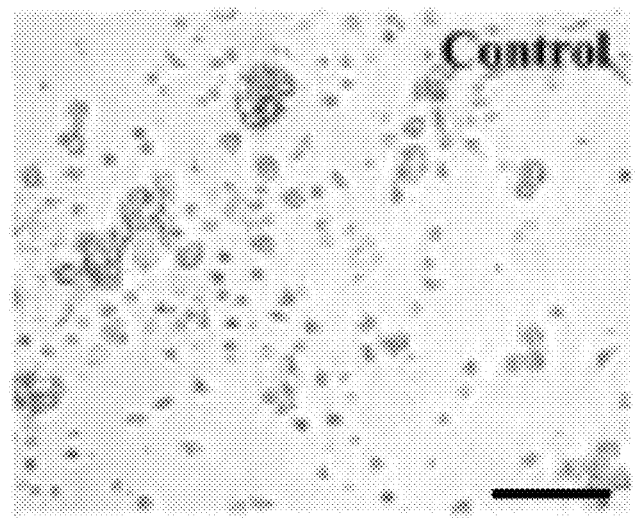
FIG. 9(D) is a microscope image showing PHA-induced proliferation of MNCs isolated from peripheral blood from a healthy control individual, in Medium 2 (containing hUCBP). Images show decreased numbers of colonies in Medium 2. Scale bar is 100 μm.
Figure 10:
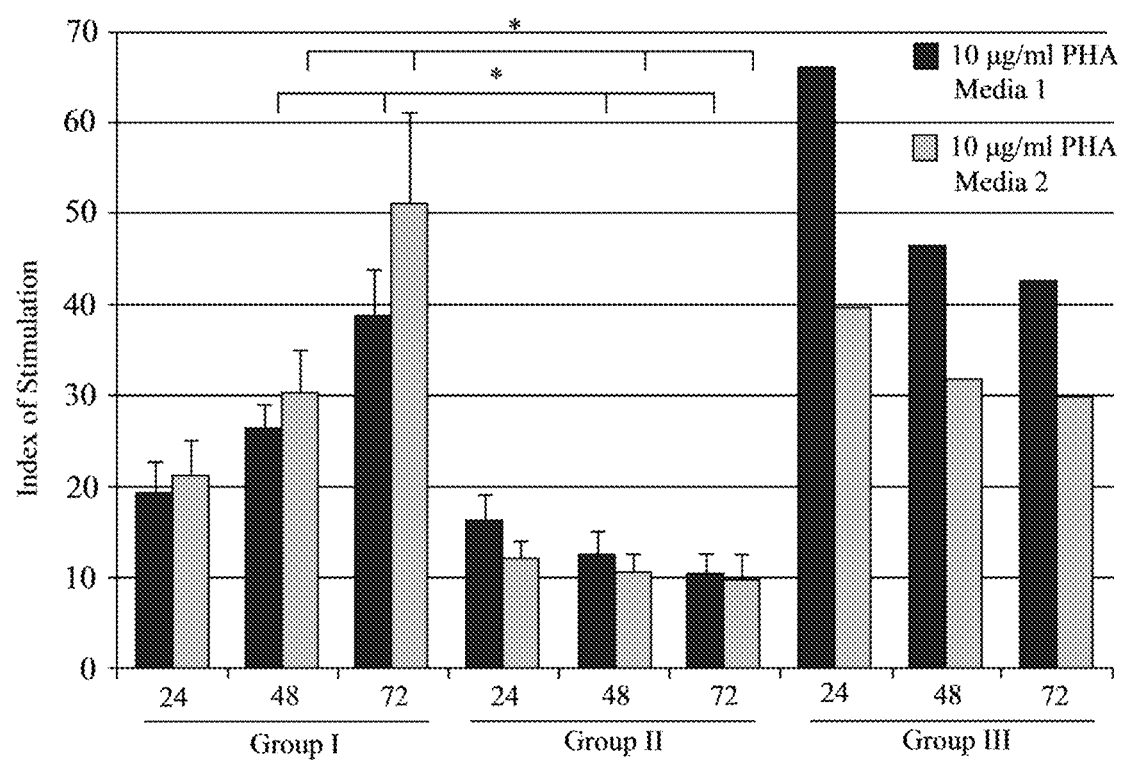
FIG. 10 is a graph showing PHA-induced proliferation of MNCs isolated from peripheral blood in Medium 1 (containing FBS) and Medium 2 (containing hUCBP). Splitting the ALS patients into the previous 3 groups based on their response to PHA in media 1, demonstrated that the proliferation response of cells to PHA (10 μg/mL) was blunted in cells exhibiting abnormal extensive proliferation (Group III) when cultured in Medium 1. An insignificant increase in cell proliferation was observed in cultures with a "normal" response to PHA (Group I) and no significant differences between Media 1 and Media 2 were found in cell cultures with non-inducible proliferation (Group II). Group II remained significantly different from control and Group I with Medium 2 (* p<0.05).

Isolated MNCs cultured with media supplemented with plasma collected from hUCB (Medium 2) and treated with PHA showed a non-significant increase in the IS after incubating on Medium 2 at each point. In the healthy control population, the difference in index of stimulation between media and plasma-supplemented media increased as time progressed, with a difference under 5 at 24 hours and about 10 by 72 hour, as seen in FIG. 8. Cells from all ALS patients appeared to exhibit a mild time-dependent IS response, which was significantly lower than that for the control MNCs at 48 and 72 hrs. However, segregating the ALS population based on PHA response, as undertaken in Example 3, revealed that stimulation of the cells that exhibited abnormal extensive proliferation (Group III) using Medium 1 resulted in clustering of Group III cells, not seen in the control group, as seen in FIGS. 9(A) and 9(B). By comparison, the UCB plasma-supplemented medium (Medium 2) showed a blunted expansion, as seen in FIG. 9(C), compared to the control group seen in FIG. 9(D). The modulated stimulation effect seen with Medium 2 was observed at all time points, as seen in FIG. 10. Insignificant increases were observed in cultures with a standard response to PHA (Group I; n=5), while no differences between Medium 1 and Medium 2 were observed from cell cultures that exhibited non-inducible proliferation (Group II). Group II MNCs had a significantly lower index of stimulation than Group I and controls at both 48 and 72 hours with regards to Medium 2. Again, no differences were observed when the patients were grouped by ALSFRS and no correlations were evident.

ALS patients differed in lymphocyte functionality, possible due to differences in immune response. Patients with abnormally extensive cell proliferation (Group III) in response to mitogen (PHA) in vitro probably have autoimmunity impairment while non-inducible proliferation (Group II) may indicate immune deficiency. Cord blood plasma modulates the cell response to the mitogen (PHA) only in patients with abnormally extensive cell proliferation and was not effective in patients with non-inducible cell proliferation.

These initial results demonstrate that plasma derived from cord blood could be effective in ALS patients with immune dysfunction.

Example 5

Caspase 3/7 activity was determined in MNCs isolated from the peripheral blood of ALS patients to determine the potential of these cells to undergo apoptosis. MNCs isolated from the peripheral blood of ALS patients and healthy volunteers, as described in Example 3. The MNCs were plated and incubated in Medium 1 as described above for 5 days, after which the cells were incubated in Medium 2 for 24 hrs. Caspase 3/7 activities were determined in these cells using a Magic Red Caspase 3/7 kit (Immunochemistry Technologies, LLC, Bloomington, Minn., USA). Briefly, 10 µL of the 31× Magic Red-(aspartate-glutamate-valine-aspartate), $[MR-(DEVD)^2]$ solution was added to each cell well and incubated for 1 hour. Hoechst dye (nuclei staining; Sigma-Aldrich) was added at 1 µL/well and incubated for an additional 5 min. Immediately after incubation, five representative photomicrographs were produced and counts of Caspase 3/7- and Hoechst-positive cells were performed using ImagePro Software. Apoptotic Caspase 3/7 cells were expressed as the percentage of the total Hoechst cells.

Data are presented as mean±S.E.M. The results were evaluated using ANOVA and Tukey's post hoc test or a paired Student's t-test (Excel; Microsoft, Redmond, Wash., USA). A p value <0.05 was considered significant.

Figure 11:
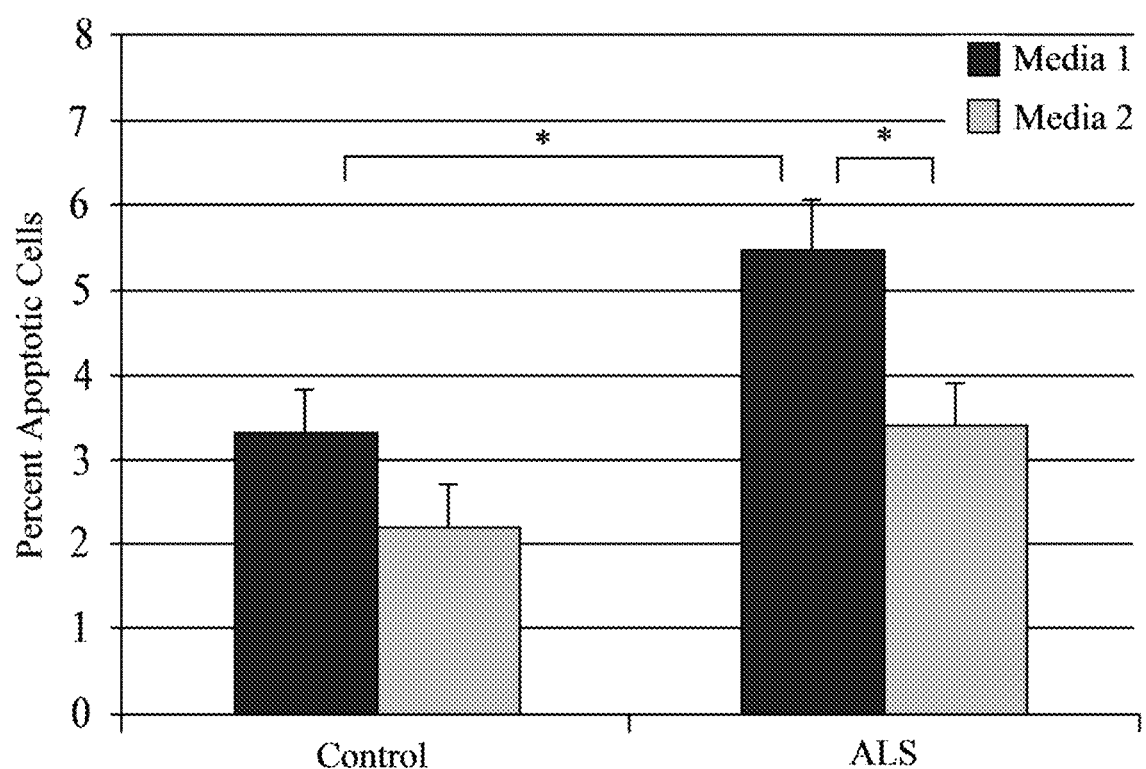
FIG. 11 is a graph showing caspase 3/7 activity in MNCs isolated from the peripheral blood of ALS patients. Many Caspase-3/7-positive cells were found in the MNCs of ALS patients cultured for 5 days in Medium 1, which was significantly different from that in controls (* p<0.05). When Medium 1 was changed to Medium 2 containing hUCB plasma for 24 hrs, the apoptotic activity of cells in the ALS patients was significantly lower than ion medium 1(p<0.05).
Figure 12:
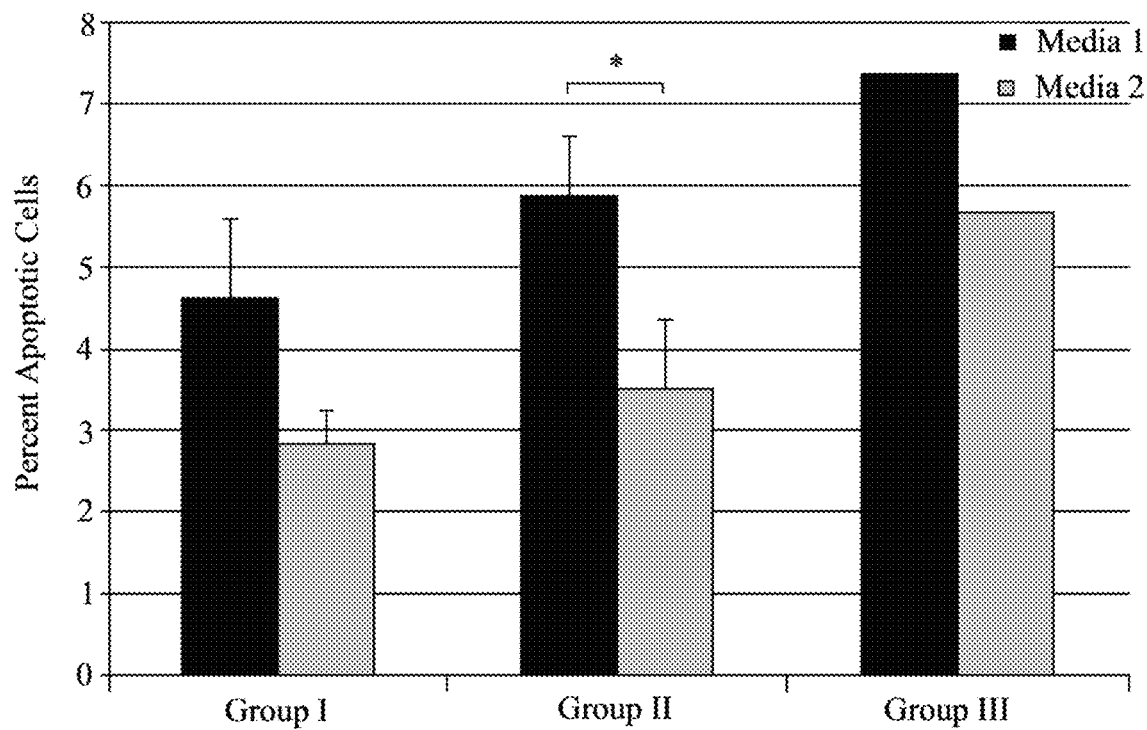
FIG. 12 is a graph showing caspase 3/7 activity in MNCs isolated from the peripheral blood of ALS patients. More Caspase-3/7-positive cells were found in patients with abnormal extensive proliferation (Group III) and non-inducible proliferation (Group II) compared to patients with "normal" response to PHA (Group I), though this was not significant. Cultured MNCs in Medium 2 showed significantly decreased apoptotic activity in patients with an abnormal response to PHA stimulation (p<0.05).
Figure 13A:
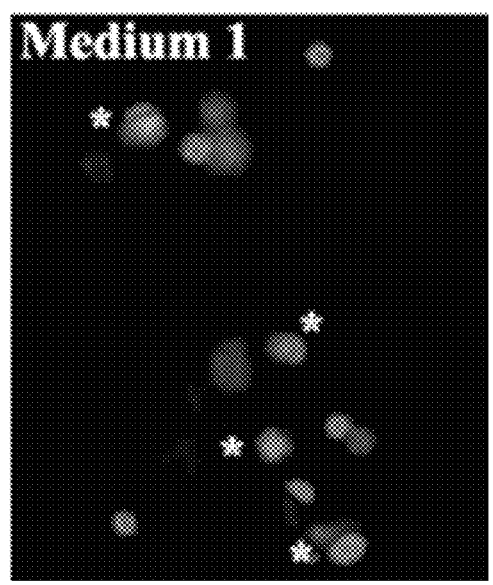
FIG. 13(A) is a microscopic image showing caspase 3/7 activity in MNCs isolated from the peripheral blood of ALS patients. Images show the numbers of Caspase 3/7 positive cells in Medium 1 (Group III) (red, asterisks). The nuclei are stained with Hoechst. Magnification is 20×.
Figure 13B:
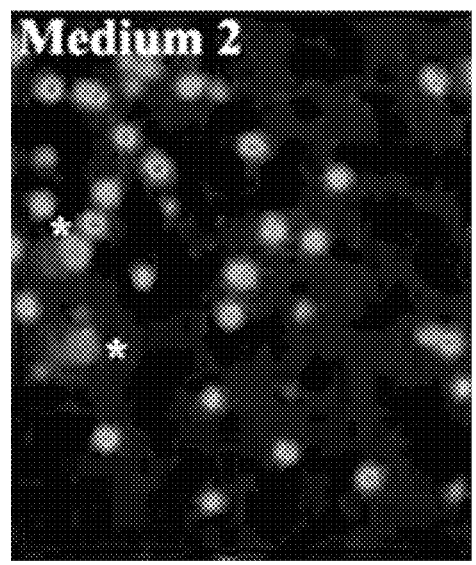
FIG. 13(B) is a microscopic image showing caspase 3/7 activity in MNCs isolated from the peripheral blood of ALS patients. Images show the decreased numbers of Caspase 3/7 positive cells in Medium 2 (Group III) (red, asterisks). The nuclei are stained with Hoechst. Magnification is 20×.

MNCs, isolated from ALS patients, cultured in medium 1 showed many caspase 3/7-positive cells with significantly more pronounced expression in cells compared to controls (p<0.05), as seen in FIG. 11. The increase in caspase-3 and 7-positive cells was more pronounced in in patients with abnormal extensive proliferation (7.38%, Group III), and non-inducible proliferation (5.81%, Group II), compared to patients with "normal" response to PHA (4.58%, Group I) or MNC hUCB (3.75%). Caspase activity of the ALS patients generally showed more activity in patients that exhibited abnormal extensive proliferation or non-inducible proliferation compared to MNCs that showed a normal response to PHA. Using Medium 2 supplemented with hUCB plasma resulted in significantly lower apoptotic activity after a 24 hour incubation for all ALS (p<0.05). However, group analysis suggested that only the Group 1 (ALSFRS<20) and Group 3 (ALSFRS>30) patients had significantly reduced levels of caspase 3/7 (p<0.05; data not shown). When grouped by their response to PHA, only MNCs from patients that exhibited an abnormal response to PHA stimulation, i.e. Groups II and III, showed decreased apoptotic activity (p<0.05) when cultured in Medium 2, as seen in FIG. 12. Images of the stained cells show higher numbers of cells stained positive for caspase 3 & 7 when the cells were incubated in medium 1, seen as asterisk in FIG. 13(A), compared to a decreased number of caspase 3&7 positive cells when grown in medium 2, seen as asterisk in FIG. 13(B).

Figure 14:
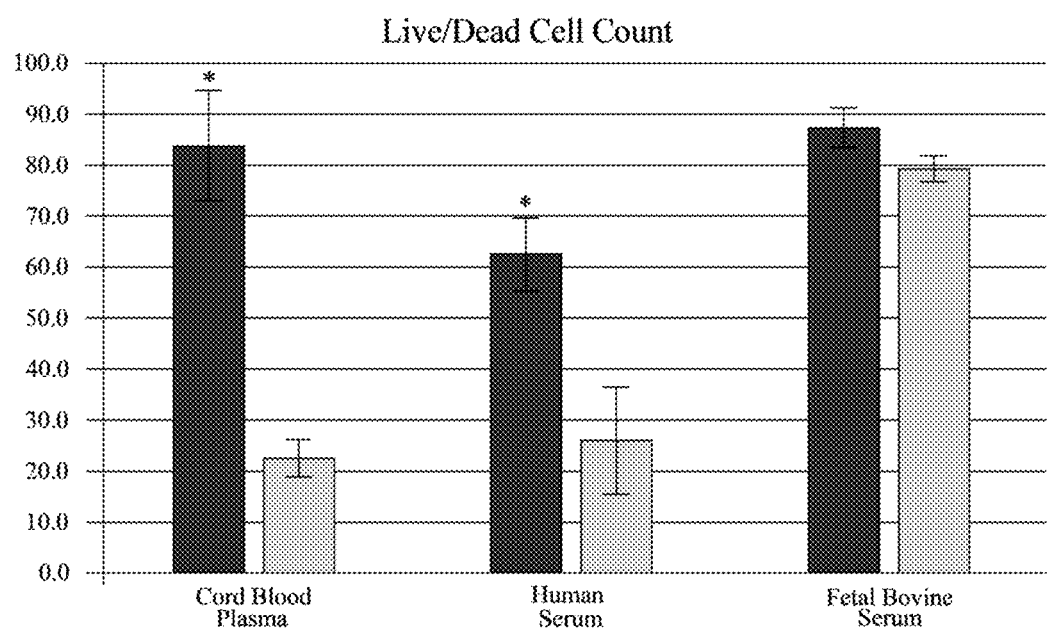
FIG. 14 is a graph showing cord blood plasma decreases cell death in vitro. Human umbilical cord blood cells were cultured in media supplemented with either cord blood plasma (CB Plasma), adult human serum (HS) or fetal bovine serum (FBS). Cells cultured in cord blood plasma demonstrated significantly greater live (dark gray) to dead (light gray) cells, compared to other groups using a Live/Dead viability assay kit. Cord blood plasma provided a beneficial environment that not only supported cell survival with greater viability. Results are plotted as mean±SEM. Statistical significance was determined using two tailed t-tests (* p<0.001).
Figure 15:
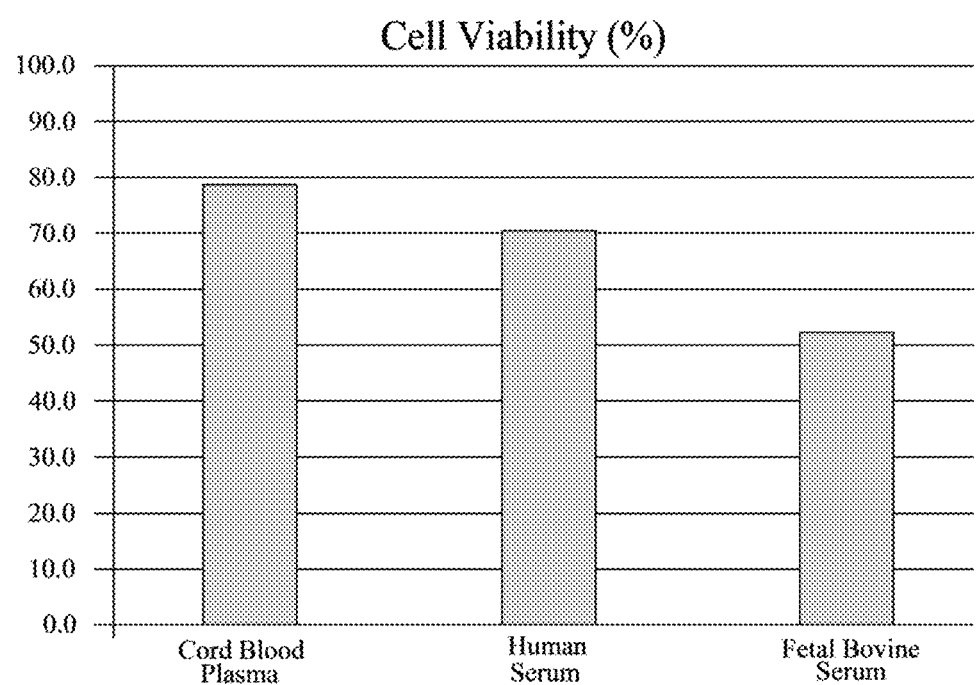
FIG. 15 is a graph showing cord blood plasma decreases cell death in vitro. Human umbilical cord blood cells were cultured in media supplemented with either cord blood plasma (CB Plasma), adult human serum (HS) or fetal bovine serum (FBS). Viability of cells in CB plasma supplemented media was better in comparison to cultures supplemented with either HS or FBS. Cord blood plasma provided a beneficial environment that not only supported cell survival with greater viability.

Cell viability was then tested against other blood serum. hUCB cells were collected as discussed in Example 1. The cells were cultured in media supplemented with cord blood plasma, adult human serum (human serum), or fetal bovine serum (FBS). Cells were incubated for 3 days, followed by a PBS wash and analysis of viability using the commercially available LIVE/DEAD cell vaiaiblity assay (TheroFisher Scientific, Cat. No. L3224). Six random fields were selected and images by confocal microscopy for each growth condition. As seen in FIG. 14, cells grown in human serum possessed the lowest number of live cells, with around 62 live cells identified. By comparison, cells grown in cord blood plasma and fetal bovine serum were found to have around 85 live cells and 88 live cells, respectively. The number of dead cells was found to be the highest in fetal bovine serum-supplemented media, followed by human serum and cord blood, at 79 cells, around 25 cells, and around 22 cells, respectively. This resulted in a ratio of live to dead cells of 3.7:1 for cord blood plasma, 2.4:1 for human serum, and 1.1:1 for fetal bovine serum. Cell viability was calculated, following a similar pattern, with cord blood showing viability of around 79%, 70% for human serum, and around 52% for fetal bovine serum, as seen in FIG. 15.

Cord blood plasma decreased apoptotic Caspase 3&7 activity in MNCs isolated from the peripheral blood of patients with both abnormal extensive or non-inducible cell proliferation to the mitogen (PHA).

Example 6

Intravenous administration of hUCB cells delayed the progression of disease and prolonged lifespan in the G93A SOD1 mouse model of ALS (Garbuzova-Davis, et al., Multiple intravenous administrations of human umbilical cord blood cells benefit in a mouse model of ALS. PLoS One 7(2):e31254; 2012; Garbuzova-Davis, et al., Human umbilical cord blood treatment in a mouse model of ALS: optimization of cell dose. PLoS One 3(6):e2494; 2008; Garbuzova-Davis, et al., Intravenous administration of human umbilical cord blood cells in a mouse model of amyotrophic lateral sclerosis: distribution, migration, and differentiation. J. Hemather. Stem Cell Res. 12(3):255-270; 2003). These results were further supported by observations of increased motor neuron survival in both the cervical and lumbar regions of the spinal cord. Also, restored WBC profiles and decreased pro-inflammatory cytokine production were determined. While these results have yet to be replicated in the clinic, the results demonstrate the therapeutic potential of using plasma derived from hUCB to mitigate the mitogen-induced proliferation response of MNCs isolated from the peripheral blood of ALS patients in vitro.

ALS patients differed in lymphocyte functionality, possibly due to differences in the immune response as a consequence of the disease state. The patient with an abnormally extensive cell proliferation in response to mitogen (PHA) in vitro (Group III) may result from an autoimmunity impairment while the non-inducible proliferation patients (Group II) suggests immune deficiency.

This suggests that use of therapies which affect the immune system may not be effective in all patients, suggesting that a more personalized medicine approach may be necessary. A recent clinical study of autologous MSCs as a treatment therapy for ALS suggested that not all patients responded to treatment (Kim, et al., Biological markers of mesenchymal stromal cells as predictors of response to autologous stem cell transplantation in patients with amyotrophic lateral sclerosis: an investigator-initiated trial and in vivo study. Stem Cells 32(10):2724-2731; 2014). A higher secretion of biological markers such as VEGF, angiopoietin and TGF-β was observed from the MSCs of those patients who responded to the treatment and this could be explored further with regards to the observations.

Innate and adaptive immune responses clearly play an important role in ALS. Infiltration of microglia and T cells is evident and it has been suggested that these cells may initially be protective (Banerjee, et al., Adaptive immune neuroprotection in G93A-SOD1 amyotrophic lateral sclerosis mice. PLoS One3(7):e2740; 2008; Beers, et al., CD4+ T cells support glial neuroprotection, slow disease progression, and modify glial morphology in an animal model of inherited ALS. Proc. Natl. Acad. Sci. USA $10^5$(40):15558-15563; 2008; Chiu, et al., T lymphocytes potentiate endogenous neuroprotective inflammation in a mouse model of ALS. Proc. Natl. Acad. Sci. USA $10^5$(46):17913-17918; 2008), but some studies have also observed lymphopenia in ALS patients or G93A SOD1 symptomatic mice (Banerjee, et al., Adaptive immune neuroprotection in G93A-SOD1 amyotrophic lateral sclerosis mice. PLoS One3(7):e2740; 2008; Kuzmenok, et al., Lymphopenia and spontaneous autorosette formation in SOD1 mouse model of ALS. J. Neuroimmunol. 172(1-2):132-136; 2006; Provinciali, et al., Immunity assessment in the early stages of amyotrophic lateral sclerosis: a study of virus antibodies and lymphocyte subsets. Acta Neurol. Scand. 78(6):449-454; 1988). However, the precise roles of the immune responses, whether causative and/or a consequence of the disease still need to be determined (Murdock, et al., The dual roles of immunity in ALS: injury overrides protection. Neurobiol. Dis. 77:1-12; 2015; Rodrigues, et al., The innate and adaptive immunological aspects in neurodegenerative diseases. J. Neuroimmunol. 269(1-2):1-8; 2014). While there is no doubt that the immune system is involved in ALS, it is worth noting that immunosuppressive therapies for ALS are not very effective (Pagani, et al., Autoimmunity in amyotrophic lateral sclerosis: past and present. Neurol. Res. Int. 2011:497080; 2011). There is evidence for autoimmunity being a component of ALS, though it is unclear whether it is causative or an epiphenomenon (Alexianu, The role of immune processes in amyotrophic lateral sclerosis pathogenesis. Rom. J. Neurol. Psychiatry 33(3-4):215-227; 1995; Appel, et al., Autoimmunity as an etiological factor in sporadic amyotrophic lateral sclerosis. Adv. Neurol. 68:47-57; 1995; Coban, et al., Serum anti-neuronal antibodies in amyotrophic lateral sclerosis. Int. J. Neurosci. 123(8):557-562; 2013; Niebroj-Dobosz, et al., Auto-antibodies against proteins of spinal cord cells in cerebrospinal fluid of patients with amyotrophic lateral sclerosis (ALS). Folia Neuropathol. 44(3):191-196; 2006; Pagani, et al., Autoimmunity in amyotrophic lateral sclerosis: past and present. Neurol. Res. Int. 2011:497080; 2011; Rodrigues, et al., The innate and adaptive immunological aspects in neurodegenerative diseases. J. Neuroimmunol. 269(1-2):1-8; 2014), with some suggestion that autoimmunity could be beneficial in chronic neuroinflammation (Schwartz & Baruch, Breaking peripheral immune tolerance to CNS antigens in neurodegenerative diseases: boosting autoimmunity to fight-off chronic neuroinflammation. J. Autoimmun. 54:8-14; 2014). Serum, CSF and immune cells from ALS patients has also been shown to contain increased levels of IL-17 and IL-23, which may be a sign of T helper 17 (Th17) cell activation—a cell type that may play a crucial role in destructive autoimmunity (Fiala, et al., IL-17A is increased in the serum and in spinal cord CD8 and mast cells of ALS patients. J. Neuroinflammation 7:76; 2010; Rentzos, et al., Interleukin-17 and interleukin-23 are elevated in serum and cerebrospinal fluid of patients with ALS: a reflection of Th17 cells activation? Acta Neurol Scand. 122(6):425-429; 2010; Saresella, et al., T helper-17 activation dominates the immunologic milieu of both amyotrophic lateral sclerosis and progressive multiple sclerosis. Clin. Immunol. 148(1):79-88; 2013).

While the study demonstrated impairment of mononuclear cells obtained from the peripheral blood of ALS patients via mitogen induction, Bossolasco et al. (Bossolasco, et al., Metalloproteinase alterations in the bone marrow of ALS patients. J. Mol. Med. 88(6):553-564; 2010) have detected impaired functionality of bone marrow stem cells (BMSCs) from ALS patients in the ability to proliferate and differentiate into adipogenic and osteoblastic tissue, though Ferrero et al. (Ferrero, et al., Bone marrow mesenchymal stem cells from healthy donors and sporadic amyotrophic lateral sclerosis patients. Cell Transplant. 17(3):255-266; 2008) noted no significant differences in the proliferation potential of bone marrow mesenchymal stem cells from ALS patients. Liu and Martin (Liu, & Martin, The adult neural stem and progenitor cell niche is altered in amyotrophic lateral sclerosis mouse brain. J. Comp. Neurol. 497(3):468-88; 2006) showed a similar impairment of neural stem cells (NSCs) in the subventricular zone of symptomatic G93A SOD1 mice. These studies suggested that some cell populations, such as the peripheral blood lymphocytes and possibly the BMSCs, undergo changes in their ability to proliferate and/or differentiate in ALS patients, however, no reports exist to confirm any abnormal cell function. Though Kang et al. (Kang, et al., Degeneration and impaired regeneration of gray matter oligodendrocytes in amyotrophic lateral sclerosis. Nat. Neurosci. 16(5):571-579; 2013) have detected enhanced proliferation of non-stimulated oligodendrocytic progenitors in the G93A SOD1 transgenic mouse.

The findings demonstrated that cord blood plasma was effective at modulating the cell response to PHA in the patient with abnormally extensive cell proliferation (Group III) as well as the patients with non-inducible cell proliferation (Group II), but not the patients who responded normally (Group I). Also, hUCBP decreased apoptotic Caspase 3/7 activity in MNCs isolated from the peripheral blood of patients with both abnormal extensive or non-inducible cell proliferation to the mitogen (PHA). Additionally, when standard media (Medium 1) was replaced with media containing hUCBP (Medium 2) the apoptotic activity of the MNCs in culture tended to decrease. These findings reinforce the current anti-inflammatory observations that have been made of hUCB cells (Garbuzova-Davis, et al., Multiple intravenous administrations of human umbilical cord blood cells benefit in a mouse model of ALS. PLoS One 7(2): e31254; 2012), and also demonstrate that plasma derived from cord blood could be an effective treatment in ALS patients with immune dysfunction as an immune-modulator and/or anti-apoptotic factor.

ALSFRS/ALSFRS-R scoring of ALS patients is a well-recognized and widely used standard in ALS clinics to validate patient disease stage. Although the testing methodology might be subjective, all the data was collected by the same neurologist in order to minimize the potential for bias. The scores were then calculated using the on-line ALS C.A.R.E. program (Center for Outcomes Research, Univ Massachusetts Medical School, 2015).

Although the patient sample size in the study was modest, it was sufficient to provide a valid analysis of hUCB plasma effects on mitogen-induced proliferation of MNCs isolated from the peripheral blood of ALS patients. Additionally, the significant reduction of apoptotic activity of these cells via hUCB plasma is an important study finding.

The therapeutic uses of hUCB plasma (hUCBP) are shown for ALS. hUBCP modulates immune cell response to stimulation with the mitogen PHA. Also, hUCBP is a novel therapy that appears to correct any immunological issues that arise from ALS. This therapy can be combined with hUCB cell (or other cell) transplants to potentially help provide a more supportive environment for the transplanted cells.

In the preceding specification, all documents, acts, or information disclosed do not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

It is also to be understood that the following claims are intended to cover all of the generic and specific features of the invention herein described, and all statements of the scope of the invention which, as a matter of language, might be said to fall there between.

What is claimed is:

1. A method of mitigating a mitogen-induced proliferation response of mononuclear cells from an amyotrophic lateral sclerosis (ALS) patient, comprising the steps:
    isolating mononuclear cells from peripheral blood of the ALS patient;
    incubating the mononuclear cells of the patient with a mitogen;
    assaying proliferation of the mononuclear cells incubated with the mitogen over a period of time using a proliferation assay and comparing the proliferation of the mononuclear cells to a control;
    wherein abnormally extensive cell proliferation is established by a showing of increased stimulation of the incubated mononuclear cells with a decreasing trend over time as compared to the control;
    wherein, if the mononuclear cells of the patient exhibit abnormally extensive cell proliferation in response to the mitogen, obtaining plasma derived from umbilical cord blood; and contacting the mononuclear cells with an effective amount of the plasma derived from umbilical cord blood; thereby mitigating the mitogen-induced proliferation response of the mononuclear cells from the ALS patient.

2. The method of claim 1, wherein the patient is identified as suffering from ALS using ALS Functional Rating Scale or ALS Functional Rating Scale-revised.

3. The method of claim 1, wherein the plasma derived from umbilical cord blood is derived from human umbilical cord blood.

4. The method of claim 1, further comprising: administering a therapeutic composition to the ALS patient whose mononuclear cells exhibit abnormal extensive proliferation, wherein the composition is riluzole, mesenchymal stem cells, umbilical cord blood cells, or a combination thereof.

5. The method of claim 4, wherein the umbilical cord blood cells are a mononuclear cell fraction.

6. The method of claim 4, wherein the composition is a composition of $CD34^+$ cells.

7. The method of claim 5, wherein the umbilical cord blood cells are administered at about $1\times10^4$ to about $5\times10^7$ cells.

8. The method of claim 5, wherein the umbilical cord blood cells are administered at about $0.1\times10^6$ cells/kg to about $10\times10^8$ cells/kg.

9. The method of claim 8, wherein the umbilical cord blood cells are administered at about $0.5\times10^8$ cells/kg.

10. The method of claim 1, further comprising administering the plasma derived from umbilical cord blood, obtained in claim 1, to the ALS patient having mononuclear cells exhibiting abnormal extensive proliferation wherein the plasma derived from umbilical cord blood is administered at about 10 ml/kg to about 20 ml/kg.

* * * * *